US010100283B2

(12) United States Patent
Tsumaki

(10) Patent No.: US 10,100,283 B2
(45) Date of Patent: Oct. 16, 2018

(54) EFFICIENT CHONDROCYTE INDUCTION METHOD

(71) Applicant: KYOTO UNIVERSITY, Kyoto (JP)

(72) Inventor: Noriyuki Tsumaki, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 3 days.

(21) Appl. No.: 15/032,705

(22) PCT Filed: Oct. 31, 2014

(86) PCT No.: PCT/JP2014/079117
§ 371 (c)(1),
(2) Date: Apr. 28, 2016

(87) PCT Pub. No.: WO2015/064754
PCT Pub. Date: May 7, 2015

(65) Prior Publication Data
US 2016/0251623 A1    Sep. 1, 2016

(30) Foreign Application Priority Data

Nov. 1, 2013 (JP) ................................ 2013-228822
May 20, 2014 (JP) ................................ 2014-104162

(51) Int. Cl.
*C12N 5/077* (2010.01)
*A61K 35/32* (2015.01)

(52) U.S. Cl.
CPC ............ *C12N 5/0655* (2013.01); *A61K 35/32* (2013.01); *C12N 2500/25* (2013.01); *C12N 2500/38* (2013.01); *C12N 2501/115* (2013.01); *C12N 2501/15* (2013.01); *C12N 2501/155* (2013.01); *C12N 2501/16* (2013.01); *C12N 2501/19* (2013.01); *C12N 2501/415* (2013.01); *C12N 2506/45* (2013.01); *C12N 2513/00* (2013.01); *C12N 2533/54* (2013.01)

(58) Field of Classification Search
CPC .............. C12N 5/0655; C12N 2501/15; C12N 2501/155; C12N 2501/19; C12N 2506/45; C12N 2513/00; C12N 2501/415; C12N 2501/16; C12N 2533/54; C12N 2500/25; C12N 2500/38; C12N 2501/115; A61K 35/32
See application file for complete search history.

(56) References Cited

U.S. PATENT DOCUMENTS

| | | |
|---|---|---|
| 2008/0070303 A1 | 3/2008 | West et al. |
| 2010/0184033 A1 | 7/2010 | West et al. |
| 2011/0229440 A1 | 9/2011 | Dealy et al. |
| 2012/0171171 A1 | 7/2012 | West et al. |
| 2013/0115673 A1 | 5/2013 | West et al. |
| 2013/0315876 A1 | 11/2013 | Dealy et al. |
| 2014/0178994 A1 | 6/2014 | West et al. |
| 2016/0251623 A1* | 9/2016 | Tsumaki ...................... 424/93.7 |

FOREIGN PATENT DOCUMENTS

| | | |
|---|---|---|
| JP | 2011-041472 | 3/2011 |
| JP | 2012-533571 | 12/2012 |
| JP | 2013-511987 | 4/2013 |

OTHER PUBLICATIONS

Wei Y. et al., "Chondrogenic Differentiation of Induced Pluripotent Stem Cells From Osteoarthritic Chondrocytes in Alginate Matrix", European Cells and Materials, 2012, vol. 23, pp. 1-12.*
Extended European Search Report dated Mar. 9, 2017 in corresponding European Application No. 14857348.8.
Guzzo et al., "Efficient Differentiation of Human iPSC-Derived Mesenchymal Stem Cells to Chondroprogenitor Cells", Journal of Cellular Biochemistry, vol. 114, No. 2, 2013, pp. 480-490.
Yoon et al., "Enhanced Cartilage Formation via Three-Dimensional Cell Engineering of Human Adipose-Derived Stem Cells", Tissue Engineering: Part A, vol. 18, Nos. 19-20, 2012, pp. 1949-1956.
Yamashita et al., "Identification of Five Developmental Processes during Chondrogenic Differentiation of Embryonic Stem Cells", PLOS ONE, vol. 5, No. 6, 2010, pp. 1-11.
Outani et al., "Direct Induction of Chondrogenic Cells from Human Dermal Fibroblast Culture by Defined Factors", PLOS ONE, vol. 8, No. 10, 2013, pp. 1-12.
Wei et al., "Chondrogenic Differentiation of Induced Pluripotent Stem Cells From Osteoarthritic Chondrocytes in Alginate Matrix", European Cells and Materials, vol. 23, 2012, pp. 1-12.
Chen et al., "In Vitro Stage-Specific Chondrogenesis of Mesenchymal Stem Cells Committed to Chondrocytes", Arthritis & Rheumatism, vol. 60, No. 2, 2009, pp. 450-459.
Yamashita et al., "Generation of Scaffoldless Hyaline Cartilaginous Tissue from Human iPSCs", Stem Cell Reports, vol. 4, No. 3, 2015, pp. 404-418.
S. Roberts, et al., Immunohistochemical study of collagen types I and II and procollagen IIA in human cartilage repair tissue following autologous chondrocyte implantation, The Knee, vol. 16, pp. 398-404, 2009.
K. Mithoefer, et al., "Clinical Efficacy of the Microfracture Technique for Articular Cartilage Repair in the Knee: An Evidence-Based Systematic Analysis", The American Journal of Sports Medicine, vol. 37, No. 10, pp. 2053-2063, 2009.
Noriaki Koyama, et al., "Human Induced Pluripotent Stem Cells Differentiated into Chondrogenic Lineage Via Generation of Mesenchymal Progenitor Cells", Stem Cells and Development, vol. 22, No. 1, pp. 102-113, 2013.

(Continued)

*Primary Examiner* — Satyendra K Singh
(74) *Attorney, Agent, or Firm* — Wenderoth, Lind & Ponack, L.L.P.

(57) ABSTRACT

Provided is a method for producing chondrocytes from pluripotent stem cells, the method comprising the steps of: (i) inducing pluripotent stem cells to differentiate into mesodermal cells in adherent culture, (ii) culturing the cells obtained by step (i) in adherent culture in a medium containing one or more substances selected from the group consisting of BMP2, TGFβ and GDF5, and (iii) culturing the cells obtained by step (ii) in suspension culture in a medium containing one or more substances selected from the group consisting of BMP2, TGFβ and GDF5. Also provided is a pharmaceutical product comprising the chondrocytes obtained by the method.

10 Claims, 12 Drawing Sheets
Specification includes a Sequence Listing.

(56) References Cited

OTHER PUBLICATIONS

Nathaniel S. Hwang, et al., "Derivation of Chondrogenically-Committed Cells from Human Embryonic Cells for Cartilage Tissue Regeneration", PLOS one, vol. 3, pp. 1-10, e2498, 2008.
R. A. Oldershaw, et al., "Directed differentiation of human embryonic stem cells toward chondrocytes", Nature Biotechnology, vol. 28, No. 11, pp. 1187-1194, 2010.
H. Y. Bai, et al., "Three step derivation of cartilage like tissue from human embryonic stem cells by 2D-3D sequential culture in vitro and further implantation in vivo on alginate/PLGA scaffolds", Journal of Biomedical Materials Research Part A, vol. 94A, pp. 539-546, 2010.
A. Yamashita, et al, "Cartilage tissue engineering identifies abnormal human induced pluripotent stem cells", Scientific Reports, 3, pp. 1-6, 2013.
A. Yamashita, et al., "Development of regenerative therapy using iPS cell-derived chondrocytes", Pharma Medica, vol. 31, No. 4, pp. 29-32, 2013 (with partial English translation).
J. T. Taiani, et al., "Reduced Differentiation Efficiency of Murine Embryonic Stem Cells in Stirred Suspension Bioreactors", Stem Cells and Development, vol. 19, No. 7, pp. 989-998, 2010.
International Preliminary Report on Patentability dated May 12, 2016 in International Application No. PCT/JP2014/079117.

\* cited by examiner

SEQUENCE LISTING

```
<160> NUMBER OF SEQ ID NOS: 36

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
tggcaccaca ccttctacaa tgagc                                      25

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
gcacagcttc tccttaatgt cacgc                                      25

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gacaacaatg agaaccttca                                            20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ttctggcgcc ggttacagaa                                            20

<210> SEQ ID NO 5
<211> LENGTH: 20
<212> TYPE: DNA
<213> ORGANISM: Artificial Sequence
```

```
<220> FEATURE:
<223> OTHER INFORMATION: Primer

<400> SEQUENCE: 5
caaaggcaaa caacccactt                                              20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ctggatgttc tgggtctggt                                              20

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
tatgagcctc gaatccacat agt                                          23

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
cctcgttctg ataagcagtc ac                                           22

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
ggcccaataa tcagagtggc a                                            21

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
ccagtgtcat ttccgatcac ttt                                          23

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
cagccagagt tagcacaata gg                                           22
```

```
<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ctgttgttcc cgtcggagtt                                               20

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
ggatgcaatg acccaggatt t                                             21

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
tgaatggtac tgacaagtgt tgg                                           23

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
agacctttgg gctgccttat                                               20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tagcctccct cactccaaga                                               20

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
tgaggagggc tggaacaagt acc                                           23

<210> SEQ ID NO 18
<211> LENGTH: 23
<212> TYPE: DNA
<213> ORGANISM: Artificial Sequence
<220> FEATURE:
<223> OTHER INFORMATION: Primer
```

<400> SEQUENCE: 18
ggaggtggta attgcaggga aca                                        23

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tttcccaggt caagatggtc                                            20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
cttcagcacc tgtctcacca                                            20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
tgtgatgact acggggacaa                                            20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
ccatattcct ctgcctggaa                                            20

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
aaagtcagca catctcccaa g                                          21

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
gtgtctcttt agcggaagta gtc                                        23

```
<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
aactcgctgg ctatctcggt                                                   20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gccctcataa tgcagggact                                                   20

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
atgctgccac aaataccctt t                                                 21

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28
ggtagtgggc cttttatgcc t                                                 21

<210> SEQ ID NO 29
<211> LENGTH: 19
<212> TYPE: DNA
<213> ORGANISM: Artificial Sequence
<220> FEATURE:
<223> OTHER INFORMATION: Primer

<400> SEQUENCE: 29
gtcgagggcc aagacgaag                                                    19

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
cagatcacgt catcgcacaa c                                                 21

<210> SEQ ID NO 31
<211> LENGTH: 21
<212> TYPE: DNA
<213> ORGANISM: Artificial Sequence
<220> FEATURE:
<223> OTHER INFORMATION: Primer
```

```
<400> SEQUENCE: 31
aattggagct gttggtaacg c                                              21

<210> SEQ ID NO 32
<211> LENGTH: 19
<212> TYPE: DNA
<213> ORGANISM: Artificial Sequence
<220> FEATURE:
<223> OTHER INFORMATION: Primer

<400> SEQUENCE: 32
caccagtaag gccgtttgc                                                 19

<210> SEQ ID NO 33
<211> LENGTH: 19
<212> TYPE: DNA
<213> ORGANISM: Artificial Sequence
<220> FEATURE:
<223> OTHER INFORMATION: Primer

<400> SEQUENCE: 33
cactcctcgc cctattggc                                                 19

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
ccctcctgct tggacacaaa g                                              21

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
catacaatgg ggtaccttct gg                                             22

<210> SEQ ID NO 36
<211> LENGTH: 23
<212> TYPE: DNA
<213> ORGANISM: Artificial Sequence
<220> FEATURE:
<223> OTHER INFORMATION: Primer

<400> SEQUENCE: 36
gcatggacga gctgtacaag taa                                            23
```

EFFICIENT CHONDROCYTE INDUCTION METHOD

TECHNICAL FIELD

The present invention relates a method for inducing pluripotent stem cells to differentiate into chondrocytes. The present invention also relates to a therapeutic agent comprising chondrocytes produced by the method.

BACKGROUND ART

Cartilage tissue forms the nose, ears and joints. Cartilage tissue is composed of chondrocytes and a specific extracellular matrix that contains types II, IX, and XI collagen and proteoglycans, but not type I collagen. Cartilage tissue damaged by joint injury etc. does not spontaneously cure itself, and the damage will deteriorate without repair treatment such as transplantation. However, cartilage repair treatment suffers from the need to obtain cartilage tissue to be transplanted into the damaged area, and cartilage from other parts of the patient's body is not always sufficient in size for repair of the damage. The required in vitro expansion of harvested chondrocytes results in differentiation toward fibroblastic cells, which are not suitable for transplantation (Non Patent Literature 1). Another proposed treatment is the administration of mesenchymal stem cells. However, mesenchymal stem cells can differentiate into multiple cell types, and the administration results in transplantation of unsuitable tissue, such as fibrous tissue expressing type I collagen and hypertrophic tissue expressing type X collagen (Non Patent Literature 2).

Currently proposed is repair treatment using induced chondrocytes from pluripotent stem cells, such as iPS and ES cells (Non Patent Literature 3 to 7). However, several problems have arisen, including the formation of fibrocartilage and teratoma. Therefore, there is a need for the development of a method for driving pluripotent stem cells to generate high-quality cartilage tissue without in vivo cancer formation.

CITATION LIST

Non Patent Literature

Non Patent Literature 1: Roberts, S., et al. Knee 16, 398-404 (2009).
Non Patent Literature 2: Mithoefer, K., et al. Am. J. Sports Med. 37, 2053-2063 (2009).
Non Patent Literature 3: Koyama, N. et al. Stem cells and development 22, 102-113 (2013).
Non Patent Literature 4: Hwang, N. S., et al. PLoS ONE 3, e2498 (2008).
Non Patent Literature 5: Oldershaw, R. A. et al. Nat. Biotechnol. 28, 1187-1194 (2010).
Non Patent Literature 6: Bai, H. Y., et al. Journal of biomedical materials research. Part A 94, 539-546 (2010).
Non Patent Literature 7: Yamashita, A. et al. Scientific Reports 3 (2013).

SUMMARY OF INVENTION

Technical Problem

An object of the present invention is to provide a method for inducing pluripotent stem cells to differentiate into chondrocytes. In particular, an object of the present invention is to provide a method for inducing differentiation into chondrocytes, the method comprising the steps of inducing pluripotent stem cells to differentiate into mesodermal cells, and inducing further differentiation by a combination of adherent culture and suspension culture in a medium containing ascorbic acid, BMP2, TGFβ and GDF5.

Solution to Problem

The inventor conducted extensive research to solve the above problems, and as a result found that the step of inducing differentiation into mesodermal cells increases the efficiency of induction of chondrocytes, and that a combination of adherent culture and suspension culture in a medium containing ascorbic acid, BMP2, TGFβ and GDF5 increases the purity of chondrocytes. That is, the inventor found, for the first time, that pluripotent stem cells can be induced to differentiate into high-quality chondrocytes. The inventor also found that the chondrocytes obtained in the above manner are successfully grafted into an animal model. Based on these findings, the inventor completed the present invention.

That is, the present invention includes the following.
[1] A method for producing chondrocytes from pluripotent stem cells, the method comprising the steps of:
(i) inducing pluripotent stem cells to differentiate into mesodermal cells in adherent culture,
(ii) culturing the cells obtained by step (i) in adherent culture in a medium containing one or more substances selected from the group consisting of BMP2, TGFβ and GDF5, and
(iii) culturing the cells obtained by step (ii) in suspension culture in a medium containing one or more substances selected from the group consisting of BMP2, TGFβ and GDF5.
[2] The method of the above [1], further comprising the step of culturing the cells obtained by step (iii) in a serum-containing medium.
[3] The method of the above [1] or [2], wherein the medium used in the steps (i), (ii) and (iii) further contains 1% FBS.
[4] The method of any one of the above [1] to [3], wherein the culture in step (iii) is suspension culture of the cells obtained by step (ii) without prior use of a detachment solution.
[5] The method of any one of the above [1] to [4], wherein the induction of differentiation into mesodermal cells in step (i) is achieved by culture in a medium containing Wnt3a and Activin A.
[6] The method of any one of the above [1] to [5], wherein step (i) takes 5 days or less.
[7] The method of any one of the above [1] to [6], wherein step (ii) takes 15 days or less.
[8] The method of any one of the above [11] to [7], wherein step (iii) takes 10 to 30 days. [9] The method of the above [6], wherein step (i) takes 3 days.
[10] The method of the above [7], wherein step (ii) takes 11 days.
[11] The method of the above [8], wherein step (iii) takes 14 to 28 days.
[12] A pharmaceutical product comprising the chondrocytes produced by the method of the above [1] to [11].
[13] The pharmaceutical product of the above [12], wherein the chondrocytes are in the form of a nodule comprising the chondrocytes and an extracellular matrix.
[14] The pharmaceutical product of the above [12] or [13], which is for treatment of articular cartilage injury.

[15] An induced chondrocyte from a pluripotent stem cell, the chondrocyte having
(1) at least 100-fold increase in COL2A1 gene expression compared with that in the pluripotent stem cell,
(2) at least 250-fold increase in SOX9 gene expression compared with that in the pluripotent stem cell, and
(3) no foreign gene introduced therein (except for genes used for iPS cell production).

[16] A cartilaginous tissue with three-dimensional structure, the cartilaginous tissue being composed of an outer membrane and inner components surrounded by the outer membrane,
the outer membrane comprising COL1 fibers but no COL2 fibers and having a thickness of 10 to 50 μm,
the inner components comprising COL11 fibers, COL2 fibers, proteoglycans and the cells of claim 15.

Advantageous Effects of Invention

According to the present invention, efficient induction of differentiation of pluripotent stem cells (e.g., iPS cells) into high-quality chondrocytes has become achievable for the first time. The chondrocytes produced by the method of the present invention can be used for regenerative medicine for cartilage.

DESCRIPTION OF EMBODIMENTS

Figure 1:
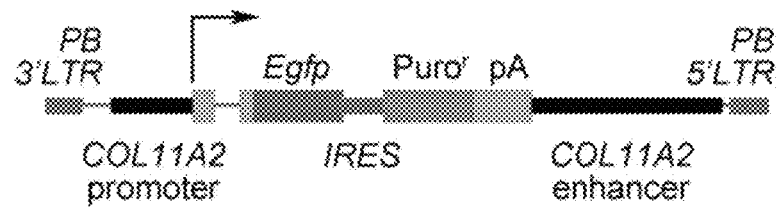
FIG. 1 shows a schematic view of Col11a2-EGFP-IRES-Puro construct expressing EGFP by the promoter activity of Col11A2.

The present invention will be described in detail below.

The present invention provides a method for producing chondrocytes from pluripotent stem cells, the method comprising the steps of:
(i) inducing pluripotent stem cells to differentiate into mesodermal cells in adherent culture,
(ii) culturing the cells obtained by step (i) in adherent culture in a medium containing one or more substances selected from the group consisting of BMP2, TGFβ and GDF5, and
(iii) culturing the cells obtained by step (ii) in suspension culture in a medium containing one or more substances selected from the group consisting of BMP2, TGFβ and GDF5.

Pluripotent stem cells that can be used in the present invention are stem cells having both pluripotency, by which the cells are capable of differentiating into any types of cells in the body, and proliferation potency. Examples of the pluripotent stem cells include, but are not limited to, embryonic stem (ES) cells, embryonic stem cells from clone embryos obtained by nuclear transplantation (nuclear transfer ES (ntES) cells), spermatogonial stem cells (germline stem (GS) cells), embryonic germ cells (EG cells), induced pluripotent stem (iPS) cells, and pluripotent cells (Muse cells) derived from cultured fibroblasts and myeloid stem cells. Preferred pluripotent stem cells are ES cells, ntES cells, and iPS cells.

(A) Embryonic Stem Cells

ES cells are stem cells having pluripotency and proliferation potency via self-replication and are established from the inner cell mass of early embryos (e.g., blastocysts) of a mammal such as a human or a mouse.

ES cells are embryo-derived stem cells originated from the inner cell mass of blastocysts, which arise from the morula after the eight-cell stage of fertilized eggs. ES cells have so-called pluripotency, by which they are capable of differentiating into any types of cells composing an adult body, and proliferation potency via self-replication. ES cells were discovered in mice in 1981 (M. J. Evans and M. H. Kaufman (1981), Nature 292:154-156). Thereafter, ES cell lines were also established in primates including humans, monkeys, etc. (J. A. Thomson et al. (1998), Science 282: 1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by harvesting the inner cell mass from blastocysts developed from fertilized eggs of a subject animal and then culturing the inner cell mass on fibroblasts as feeders. Cell maintenance by subculture can be performed using a medium supplemented with substances such as leukemia inhibitory factor (LIF) and basic fibroblast growth factor (bFGF). Methods for establishment and maintenance of human and monkey ES cells are described in, for example, U.S. Pat. No. 5,843,780; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103: 9554-9559; H. Suemori et al. (2001), Dev. Dyn., 222:273-279; H. Kawasaki et al. (2002), Proc. Natl. Acad. Sci. USA, 99:1580-1585; and Klimanskaya I, et al. (2006), Nature. 444:481-485.

Human ES cells can be maintained under humid atmosphere of 2% $CO_2$/98% air at 37° C. in a medium for preparation of ES cells, for example, a DMEM/F-12 medium supplemented with 0.1 mM 2-mercaptoethanol, 0.1 mM nonessential amino acids, 2 mM L-glutamic acid, 20% KSR, and 4 ng/ml bFGF (O. Fumitaka et al. (2008), Nat. Biotechnol., 26:215-224). ES cells need to be subcultured every 3 to 4 days. The subculture can be performed using, for example, 0.25% trypsin and 0.1 mg/ml collagenase IV in PBS containing 1 mM $CaCl_2$ and 20% KSR.

ES cells can be generally selected by using the expression of gene markers as an index, such as alkaline phosphatase, Oct-3/4 and Nanog. The markers can be detected by Real-time PCR. In particular, for selection of human ES cells, the expression of gene markers such as OCT-3/4, NANOG and ECAD can be used as an index (E. Kroon et al. (2008), Nat. Biotechnol., 26:443-452).

Human ES cell lines, for example, WA01 (HI) and WA09 (H9) are available from WiCell Research Institute, Inc., and KhES-1, KhES-2 and KhES-3 are available from the Institute for Frontier Medical Sciences, Kyoto University (Kyoto, Japan).

(B) Spermatogonial Stem Cells

Spermatogonial stem cells are testis-derived pluripotent stem cells, serving as an origin for spermatogenesis. Spermatogonial stem cells can also be induced to differentiate into cells of various lineages in a manner similar to that in ES cells. For example, spermatogonial stem cells can generate chimeric mice when transplanted into mouse blastocysts (M. Kanatsu-Shinohara et al. (2003) Biol. Reprod., 69:612-616; K. Shinohara et al. (2004), Cell, 119: 1001-1012). In addition, spermatogonial stem cells are self-replicable in a medium containing glial cell line-derived neurotrophic factor (GDNF), and spermatogonial stem cells can be maintained by repeated subculture under culture conditions similar to those for ES cells (Masancri Takebayashi et al., (2008), Experimental Medicine, Vol. 26, No. 5 (Extra Number), pp. 41-46, YODOSHA (Tokyo, Japan)).

(C) Embryonic Germ Cells

Embryonic germ cells are cells established from primordial germ cells at the prenatal period and have pluripotency similar to that of ES cells. Embryonic germ cells can be established by culturing primordial germ cells in the presence of substances such as LIF, bFGF, and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be generated by introducing specific reprogramming factors in the form of DNA or protein into somatic cells. iPS cells are somatic cell-derived artificial stem cells having properties almost equivalent to those of ES cells, such as pluripotency and proliferation potency via self-replication (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666). The reprogramming factor may be a gene specifically expressed in ES cells, a gene product or non-coding RNA thereof, a gene playing an important role in maintenance of undifferentiation of ES cells, a gene product or non-coding RNA thereof, or a low-molecular-weight compound. Examples of the genes serving as the reprogramming factors include, for example, Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, β-catenin, Lin28b, Sall1, Sall4, Esrrb, Nr5a2, Tbx3 and Glis1. These reprogramming factors may be used alone or in combination. Examples of the combination of such reprogramming factors include those described in WO 2007/069666, WO 2008/118820, WO 2009/007852, WO 2009/032194, WO 2009/058413, WO 2009/057831, WO 2009/075119, WO 2009/079007, WO 2009/091659, WO 2009/101084, WO 2009/101407, WO 2009/102983, WO 2009/114949, WO 2009/117439, WO 2009/126250, WO 2009/126251, WO 2009/126655, WO 2009/157593, WO 2010/009015, WO 2010/033906, WO 2010/033920, WO 2010/042800, WO 2010/050626, WO 2010/056831, WO 2010/068955, WO 2010/098419, WO 2010/102267, WO 2010/111409, WO 2010/111422, WO 2010/115050, WO 2010/124290, WO 2010/147395, WO 2010/147612, Huangfu D, et al. (2008), Nat. Biotechnol., 26:795-797, Shi Y, et al. (2008), Cell Stem Cell, 2: 525-528, Eminli S, et al. (2008), Stem Cells. 26:2467-2474, Huangfu D, et al. (2008), Nat Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci USA. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, Mali P, et al. (2010), Stem Cells. 28:713-720, and Maekawa M, et al. (2011), Nature. 474:225-9.

The reprogramming factors also include factors used for enhancing the establishment efficiency, such as histone deacetylase (HDAC) inhibitors [e.g., low-molecular-weight inhibitors, such as valproic acid (VPA), trichostatin A, sodium butyrate, MC 1293, and M344, and nucleic acid-based expression inhibitors such as siRNA and shRNA against HDAC (e.g., HDAC1 siRNA Smartpool (Millipore), HuSH 29-mer shRNA Constructs against HDAC1 (OriGene)], MEK inhibitors (e.g., PD184352, PD98059, U0126, SL327, and PD0325901), glycogen synthase kinase-3 inhibitors (e.g., Bio and CHIR99021), DNA methyltransferase inhibitors (e.g., 5-azacytidine), histone methyltransferase inhibitors (e.g., low-molecular-weight inhibitors such as BIX-01294, and nucleic acid-based expression inhibitors such as siRNA and shRNA against Suv39h1, Suv39h2, SetDB1 and G9a), L-channel calcium agonists (e.g., Bayk8644), butyric acid, TGFβ inhibitors or ALK5 inhibitors (e.g., LY364947, SB431542, 616453, and A-83-01), p53 inhibitors (e.g., siRNA and shRNA against p53), ARID3A inhibitors (e.g., siRNA and shRNA against ARID3A), miR-NAs such as miR-291-3p, miR-294, miR-295, and mir-302, Wnt signaling (e.g., soluble Wnt3a), neuropeptide Y, prostaglandins (e.g., prostagiandin E2 and prostaglandin J2), hTERT, SV40LT, UTF1, IRX6, GLIS1, PITX2, DMRTB1, etc. These factors used for enhancing the establishment efficiency are not distinguished from the reprogramming factors in the present invention.

The reprogramming factors may be introduced in the form of protein into somatic cells by a technique such as lipofection, fusion with a cell membrane-permeable peptide (e.g., HIV-derived TAT and polyarginine), or microinjection.

Alternatively, the reprogramming factors may be introduced in the form of DNA into somatic cells by a technique such as a technique using a vector (such as a viral vector, a plasmid vector and an artificial chromosome vector), lipofection, a technique using a liposome, or microinjection. Examples of the viral vector include retroviral vectors, lentiviral vectors (both described in Cell, 126, pp. 663-676, 2006; Cell, 131, pp. 861-872, 2007; Science, 318, pp. 1917-1920, 2007), adenoviral vectors (Science, 322, 945-949, 2008), adeno-associated viral vectors, and Sendai virus vectors (WO 2010/008054). Examples of the artificial chromosome vectors include human artificial chromosome (HAC) vectors, yeast artificial chromosome (YAC) vectors, and bacterial artificial chromosome (BAC, PAC) vectors. Examples of the plasmid vectors include plasmids for mammalian cells (Science, 322:949-953, 2008). Such a vector can contain regulatory sequences such as a promoter, an enhancer, a ribosome binding sequence, a terminator, and a polyadenylation site, so that a nuclear reprogramming factor can be expressed. The vector may further contain, if necessary, a selection marker sequence such as a drug resistance gene (e.g., a kanamycin resistance gene, an ampicillin resistance gene, and a puromycin resistance gene), a thymidine kinase gene, and a diphtheria toxin gene, and a reporter gene sequence such as a green fluorescent protein (GFP), β-glucuronidase (GUS), and FLAG. In order to remove a gene encoding a reprogramming factor or remove a promoter together with a gene encoding a reprogramming factor binding thereto after introduction of the vector into somatic cells, LoxP sequences may be inserted upstream and downstream of the region to be removed.

Alternatively, the reprogramming factors may be introduced in the form of RNA into somatic cells by a technique such as lipofection or microinjection. In order to prevent decomposition, RNAs containing 5-methylcytidine and pseudouridine (TriLink Biotechnologies) may be used (Warren L (2010), Cell Stem Cell. 7:618-630).

A culture medium for iPS cell induction includes, for example, DMEM, DMEM/F12, or DME medium containing 10 to 15% FBS (these media may further contain LIF, penicillin/streptomycin, puromycin, L-glutamine, nonessential amino acids, β-mercaptoethanol, etc. as needed) and commercially available media [e.g., a medium for mouse ES cell culture (e.g., TX-WES medium (Thromb-X)), a medium for primate ES cell culture (e.g., a medium for primate ES/iPS cells (ReproCELL)), and a serum-free medium (mTeSR (Stemcell Technology)].

An exemplary culture method is as follows. Somatic cells are brought into contact with reprogramming factors in a DMEM or DMEM/F12 medium containing 10% FBS at 37° C. in an atmosphere of 5% $CO_2$ and are cultured for about 4 to 7 days. The cells are then reseeded on feeder cells (e.g., mitomycin C-treated STO cells or SNL cells). About 10 days after contact between the somatic cells and the reprogramming factors, the cells are subjected to culture in a bFGF-containing medium for primate ES cell culture. About 30 to 45 days or more after of the contact, iPS cell-like colonies appear.

Alternatively, the cells are cultured on feeder cells (e.g., mitomycin C-treated STO cells, SNL cells, etc.) in a 10% FBS-containing DMEM medium (this media may further contain LIF, penicillin/streptomycin, puromycin, L-glutamine, nonessential amino acids, β-mercaptoethanol, etc. as needed) at 37° C. in an atmosphere of 5% $CO_2$. About 25 to 30 days or more after the start of culture, ES-like colonies appear. Desirably, instead of feeder cells, the somatic cells to be reprogrammed are used as feeder cells (Takahashi K, et al. (2009), PLoS One. 4: e8067, or WO 2010/137746), or alternatively, an extracellular matrix (e.g., laminin-5 (WO 2009/123349) or Matrigel (BD)) is used.

Alternatively, the cells may be cultured in a serum-free medium (Sun N, et al. (2009), Proc Natl Acad Sci USA. 106:15720-15725). iPS cells may be established under low oxygen conditions (oxygen concentration of 0.1 to 15%) for enhancing the establishment efficiency (Yoshida Y, et al. (2009), Cell Stem Cell. 5:237-241, or WO 2010/013845).

During the above culture, medium exchange with a fresh medium is performed once a day from day 2 after the start of culture. The number of somatic cells to undergo nuclear reprogramming is not limited, but, for example, ranges from about $5 \times 10^3$ to about $5 \times 10^8$ cells per culture dish (100 $cm^2$).

iPS cells can be selected based on the shape of the colonies. When a drug resistance gene that is expressed along with the gene expressed during somatic reprogramming (e.g., Oct3/4, Nanog) is introduced as a marker gene, established iPS cells can be selected by culturing the cells in a medium containing the relevant drug (selective medium). When a fluorescent protein gene is used as a marker gene, iPS cells of interest can be detected by observation under a fluorescence microscope. When a luminescent enzyme gene is used as a marker gene, iPS cells of interest can be detected by adding a luminescent substrate. When a chromogenic enzyme gene is used as a marker gene, iPS cells of interest can be detected by adding a chromogenic substrate.

The term "somatic cells" as used herein refers to any types of animal cells (preferably mammalian cells including human cells) other than germ cells or totipotent cells such as ova, oocytes and ES cells. Somatic cells include, but are not limited to, somatic cells of fetuses, somatic cells of neonates, and mature healthy or pathogenic somatic cells, as well as primary cultured cells, passage cells, and established cell lines. Specific example of the somatic cells include
(1) tissue stem cells (somatic stem cells), such as neural stem cells, hematopoietic stem cells, mesenchymal stem cells, dental pulp stem cells, etc.,
(2) tissue progenitor cells, and
(3) differentiated cells, such as lymphocytes, epithelial cells, endothelial cells, muscle cells, fibroblasts (skin cells etc.), hair cells, hepatocytes, gastric mucosal cells, enterocytes, splenocytes, pancreatic cells (pancreatic exocrine cells etc.), brain cells, lung cells, renal cells and adipocytes.

When iPS cells are used to generate cells to be transplanted, the iPS cells are desirably produced from somatic cells having the same or substantially the same HLA alleles as the recipient to prevent rejection. The term "substantially the same" herein means that the HLA alleles match to the extent that immune response against the transplanted cells can be inhibited by an immunosuppressant. The somatic cells have, for example, three matched HLA alleles including HLA-A, HLA-B and HLA-DR or four matched HLA alleles further including HLA-C.

(E) ES Cells Derived from Clone Embryos Generated by Nuclear Transplantation ntES (nuclear transfer ES) cells are ES cells derived from clone embryos generated by nuclear transplantation techniques, and have properties almost the same as those of fertilized egg-derived ES cells (T. Wakayama et al. (2001), Science, 292:740-743; S. Wakayama et al. (2005), Biol. Reprod., 72:932-936; J. Byrne et al. (2007), Nature, 450: 497-502). Specifically, ntES cells are ES cells established from the inner cell mass of a blastocyst from a clone embryo that is obtained via substitution of the nucleus of an unfertilized egg with the nucleus of a somatic cell. For preparation of ntES cells, nuclear transplantation techniques (J. B. Cibelli et al. (1998), Nature Biotechnol., 16: 642-646) and the above ES cell preparation techniques are used in combination (Kiyoka Wakayama et al., (2008), Experimental Medicine, Vol. 26, No. (Extra Number), pp. 47-52). In nuclear transplantation, the nucleus of a somatic cell is injected into a mammalian enucleated unfertilized egg and then the resulting cell is cultured for several hours so as to undergo reprogramming.

(F) Multilineage-Differentiating Stress Enduring Cells (Muse Cells)

Muse cells are pluripotent stem cells produced by the method described in WO 2011/007900. Specifically, Muse cells are pluripotent cells produced by subjecting fibroblasts or bone marrow stromal cells to trypsin treatment for a long period of time, preferably 8 or 16 hours, and then culturing the cells in suspension culture. Muse cells are SSEA-3 and CD105 positive.

The term "chondrocytes" used herein refers to cells that produce an extracellular matrix (such as collagen) that forms cartilage, or refers to progenitor cells of such cells. The chondrocytes may be cells expressing a chondrocyte marker, for example, type II collagen (COL2A1) or SOX9. The COL2A1 herein includes human COL2A1 genes having nucleotide sequences of NCBI accession numbers NM_001844 and NM_033150, mouse COL2A1 genes having nucleotide sequences of NCBI accession numbers NM_001113515 and NM_031163, proteins encoded by the genes, and naturally occurring variants having the same functions as those of the genes or the proteins. The SOX9 herein includes a human SOX9 gene having a nucleotide sequence of NCBI accession number NM_000346, a mouse SOX9 gene having a nucleotide sequence of NCBI accession number NM_011448, proteins encoded by the genes, and naturally occurring variants having the same functions as those of the genes or the proteins.

(i) Step of Inducing Pluripotent Stem Cells to Differentiate into Mesodermal Cells in Adherent Culture The term "mesodermal cells" herein refers to cells that occur between the endoderm and the ectoderm at the gastrula stage of animal development, and are preferably BRACHYURY positive. The BRACHYURY herein includes human BRACHYURY genes having nucleotide sequences of NCBI accession numbers NM_001270484 and NM_003181, a mouse BRACHYURY gene having a nucleotide sequence of NCBI accession number NM_009309, proteins encoded by the genes, and naturally occurring variants having the same functions as those of the genes or the proteins.

According to the present invention, the induction of pluripotent stem cells to differentiate into mesodermal cells may be achieved by any method, and, for example, is achieved by culturing pluripotent stem cells in a medium containing Activin A and a GSK-β inhibitor.

Preferably, in step (i), pluripotent stem cells are cultured in adherent culture without feeder cells. After the cell colonies reach an appropriate size (cell nodules each containing 1 to $2 \times 10^5$ cells), the medium is exchanged with a medium containing Activin A and a GSK-3β inhibitor, and culture is continued.

The adherent culture herein may be culture in a culture vessel coated with an extracellular matrix. The coating may be applied by adding a solution containing an extracellular matrix to a culture vessel, followed by appropriately removing the solution.

The extracellular matrix herein is a supramolecular assembly present outside the cells, and may be naturally occurring or artificial (recombinant). Examples of the extracellular matrix include collagens, proteoglycans, fibronectins, hyaluronic acid, tenascins, entactins, elastin, fibrillins, laminins, and fragments of these substances. These extracellular matrices may be used in combination. The extracellular matrix may be a product prepared using cells, such as BD Matrigel™. Examples of the artificial extracellular matrix include laminin fragments. The laminins herein are hetero-trimeric proteins that contain an α-chain, a β-chain and a γ-chain, and are not particularly limited in the present invention. For example, the α-chain is α1, α2, α3, α4, or α5, the β chain is β1, β2, or β3, and the γ chain is γ1, γ2, or γ3. The laminin fragments herein are not particularly limited as long as they have integrin-binding activity, and examples thereof include laminin E8 fragments produced by digesting laminins with elastase.

The medium used in step (i) may be prepared by adding Activin A and a GSK-3β inhibitor to a basal medium for animal cell culture. Examples of the basal medium include IMDM medium, Medium 199, Eagle's minimum essential medium (EMEM), αMEM medium, Dulbecco's modified Eagle's medium (DMEM), Ham's F12 medium, RPMI 1640 medium, Fischer's medium, and a mixed medium thereof. These media may contain serum (e.g., FBS) or no serum. If necessary, the media may contain one or more serum substitutes such as albumin, transferrin, KnockOut Serum Replacement (KSR) (serum substitute for FBS in ES cell culture) (Invitrogen), N2 supplement (Invitrogen), B27 supplement (Invitrogen), fatty acids, insulin, sodium selenite, collagen progenitors, trace elements, 2-mercaptoethanol, and 3'-thiolglycerol, as well as one or more substances such as lipids, amino acids, L-glutamine, GlutaMAX (Invitrogen), nonessential amino acids (NEAAs), vitamins, growth factors, low-molecular-weight compounds, antibiotics, antioxidants, pyruvic acid, buffering agents, and inorganic salts. In one embodiment of this step, the basal medium is DMEM/F12 containing insulin, transferrin, sodium selenite and 1% serum.

The Activin A in step (i) includes Activin A derived from an animal such as a human and a non-human animal and functionally modified derivatives thereof. The Activin A may be, for example, a commercially available product produced by R&D systems etc. The concentration of Activin A used in this step is 0.1 to 1000 ng/ml, preferably 1 to 100 ng/ml, more preferably 5 to 50 ng/ml, in particular 10 ng/ml.

The GSK-3β inhibitor in step (i) is not particularly limited as long as it directly or indirectly inhibits the functions of GSK-3β, for example, kinase activity. Examples of the GSK-3β inhibitor include Wnt3a, the indirubin derivative BIO (also called GSK-30 inhibitor IX (6-bromoindirubin-3'-oxime)), the maleimide derivative SB216763 (3-(2,4-dichlorophenyl)-4-(1-methyl-1H-indol-3-yl)-1H-pyrrole-2,5-dione), the phenyl α-bromomethyl ketone compound GSK-3β inhibitor VII (4-dibromoacetophenone), the cell-membrane permeable phosphopeptide L803-mts (also called GSK-3β peptide inhibitor (Myr-N-GKEAPPAPPQSpP-NH$_2$)) and the highly selective inhibitor CHIR99021 (Nature (2008) 453:519-523). These compounds are commercially available from, for example, Stemgent, Calbiochem, Biomol, etc., or may be produced in-house. A preferred GSK-3β inhibitor used in this step is Wnt3a. The Wnt3a includes Wnt3a derived from an animal such as a human and a non-human animal and functionally modified derivatives thereof. The Wnt3a may be, for example, a commercially available product produced by R&D systems etc. The concentration of the GSK-GSK-3β inhibitor used in this step may be selected by a person skilled in the art as appropriate for the type of the GSK-3β inhibitor to be used. For example, the concentration of Wnt3a used as the GSK-3β inhibitor is 0.1 to 1000 ng/ml, preferably 1 to 100 ng/ml, more preferably 5 to 50 ng/ml, in particular 10 ng/ml.

The culture temperature in step (i) is not particularly limited, but, for example, ranges from about 30° C. to about 40° C., and is preferably about 37° C. The culture is performed under an air atmosphere containing $CO_2$. The $CO_2$ concentration ranges from about 2% to 5%, and is preferably about 5%. The culture period in this step is, for example, 5 days or less, and is preferably 3 days.

(ii) Step of Culturing the Cells Obtained by Step (i) in Adherent Culture in a Medium Containing One or More Substances Selected from the Group Consisting of BMP2, TGFβ and GDF5

In this step, the medium of the cell culture in step (i) is removed and exchanged with a medium containing one or more substances selected from the group consisting of BMP2, TGFβ and GDF5. The cells in the culture in step (i) are adherent to culture dishes, and the adherent culture is continued in step (ii).

The medium used in step (ii) may be prepared by adding one or more substances selected from the group consisting of BMP2, TGFβ and GDF5 to a basal medium for animal cell culture. Preferred media are a medium containing at least TGFβ, a medium containing BMP2 and TGFβ, a medium containing ascorbic acid, BMP2 and TGFβ, a medium containing GDF5, BMP2 and TGFβ, and a medium containing ascorbic acid, BMP2, TGFβ and GDF5, and more preferred is a medium containing bFGF, ascorbic acid, BMP2, TGFβ and GDF5. Examples of the basal medium include IMDM medium, Medium 199, Eagle's minimum essential medium (EMEM), αMEM medium, Dulbecco's modified Eagle's medium (DMEM), Ham's F12 medium, RPMI 1640 medium, Fischer's medium, and a mixed medium thereof. These media may contain serum (e.g., FBS) or no serum. If necessary, the media may contain one or more serum substitutes such as albumin, transferrin, KnockOut Serum Replacement (KSR) (serum substitute for FBS in ES cell culture) (Invitrogen), N2 supplement (Invitrogen), B27 supplement (Invitrogen), fatty acids, insulin, collagen progenitors, trace elements, 2-mercaptoethanol, and 3'-thiolglycerol, as well as one or more substances such as lipids, amino acids, L-glutamine, GlutaMAX (Invitrogen), nonessential amino acids (NEAAs), vitamins, growth factors, low-molecular-weight compounds, antibiotics, antioxidants, pyruvic acid, buffering agents, and inorganic salts. In one embodiment of this step, the basal medium is DMEM containing insulin, transferrin, sodium selenite, and 1% serum.

The bFGF in step (ii) includes bFGF derived from an animal such as a human and a non-human animal and functionally modified derivatives thereof. The bFGF may be, for example, a commercially available product produced by WAKO etc. The concentration of bFGF used in this step is 0.1 to 1000 ng/ml, preferably 1 to 100 ng/ml, more preferably 5 to 50 ng/ml, in particular 10 ng/ml.

The ascorbic acid in step (ii) may be, for example, a commercially available product produced by Nakarai etc. The concentration of the ascorbic acid used in this step is 5 to 500 μg/ml, preferably 10 to 100 μg/ml, more preferably 50 μg/ml.

The BMP2 in step (ii) includes BMP2 derived from an animal such as a human and a non-human animal and functionally modified derivatives thereof. The BMP2 may be, for example, a commercially available product produced by Osteopharma etc. The concentration of BMP2 used in this step is 0.1 to 1000 ng/ml, preferably 1 to 100 ng/ml, more preferably 5 to 50 ng/ml, in particular 10 ng/ml. BMP2 may be replaced by BMP4 in the present invention.

The TGFβ in step (ii) includes TGFβ derived from an animal such as a human and a non-human animal and functionally modified derivatives thereof. The TGFβ may be, for example, a commercially available product produced by PeproTech etc. The concentration of TGFβ used in this step is 0.1 to 1000 ng/ml, preferably 1 to 100 ng/ml, more preferably 5 to 50 ng/ml, in particular 10 ng/ml.

The GDF5 in step (ii) includes GDF5 derived from an animal such as a human and a non-human animal and functionally modified derivatives thereof. The GDF5 may be, for example, a commercially available product produced by PeproTech etc. The concentration of GDF5 used in this step is 0.1 to 1000 ng/ml, preferably 1 to 100 ng/ml, more preferably 5 to 50 ng/ml, in particular 10 ng/ml.

The culture temperature in step (ii) is not particularly limited, but, for example, ranges from about 30° C. to about 40° C., and is preferably about 37° C. The culture is performed under an air atmosphere containing $CO_2$. The $CO_2$ concentration ranges from about 2% to 5%, and is preferably about 5%. The culture period in this step is, for example, 15 days or less, and is preferably 11 days.

(iii) Step of Culturing the Cells Obtained by Step (ii) in Suspension Culture in a Medium Containing One or More Substances Selected from the Group Consisting of BMP2, TGFβ and GDF5

In this step, the cells obtained in the culture in step (ii) are separated from the culture dishes and then subjected to suspension culture. The separation of the cells from the culture dishes in step (iii) is preferably achieved by mechanical means (pipetting etc.), not using a detachment solution with protease activity and/or collagenase activity (e.g., solutions containing trypsin and collagenase, such as Accutase™ and Accumax™ (Innovative Cell Technologies, Inc.)).

The term "suspension culture" herein refers to culture of cells that are in a state of being non-adherent to a culture dish. The conditions of the suspension culture are not particularly limited, but preferably the suspension culture is performed in a culture vessel without artificial treatment for enhancing the cell adhesion to the vessel (e.g., without coating treatment using an extracellular matrix etc.) or a culture vessel with artificial treatment for preventing the cell adhesion to the vessel (e.g., with coating treatment using polyhydroxyethyl methacrylate (poly-HEMA)).

The medium used in step (iii) may be prepared by adding one or more substances selected from the group consisting of BMP2, TGFβ and GDF5 to a basal medium for animal cell culture. Preferred media are a medium containing at least TGFβ, a medium containing BMP2 and TGFβ, a medium containing ascorbic acid, BMP2 and TGFβ, a medium containing GDF5, BMP2 and TGFβ, and a medium containing ascorbic acid, BMP2, TGFβ and GDF5, and more preferred is a medium containing ascorbic acid, BMP2, TGFβ and GDF5. Examples of the basal medium include IMDM medium, Medium 199, Eagle's minimum essential medium (EMEM), αMEM medium, Dulbecco's modified Eagle's medium (DMEM), Ham's F12 medium, RPMI 1640 medium, Fischer's medium, and a mixed medium thereof. These media may contain serum (e.g., FBS) or no serum. If necessary, the media may contain one or more serum substitutes such as albumin, transferrin, KnockOut Serum Replacement (KSR) (serum substitute for FBS in ES cell culture) (Invitrogen), N2 supplement (Invitrogen), B27 supplement (Invitrogen), fatty acids, insulin, collagen progenitors, trace elements, 2-mercaptoethanol, and 3'-thiolglycerol, as well as one or more substances such as lipids, amino acids, L-glutamine, GlutaMAX (Invitrogen), nonessential amino acids (NEAAs), vitamins, growth factors, low-molecular-weight compounds, antibiotics, antioxidants, pyruvic acid, buffering agents, and inorganic salts. In one embodiment of this step, the basal medium is DMEM containing insulin, transferrin, sodium selenite, and 1% serum.

The ascorbic acid in step (iii) may be, for example, a commercially available product produced by Nakarai etc. The concentration of the ascorbic acid used in this step is to 500 μg/ml, preferably 10 to 100 μg/ml, more preferably 50 μg/ml.

The BMP2 in step (iii) includes BMP2 derived from an animal such as a human and a non-human animal and functionally modified derivatives thereof. The BMP2 may be, for example, a commercially available product produced by Osteopharma etc. The concentration of BMP2 used in this step is 0.1 to 1000 ng/ml, preferably 1 to 100 ng/ml, more preferably 5 to 50 ng/ml, in particular 10 ng/ml.

The TGFβ in step (iii) includes TGFβ derived from an animal such as a human and a non-human animal and functionally modified derivatives thereof. The TGFβ may be, for example, a commercially available product produced by PeproTech etc. The concentration of TGFβ used in this step is 0.1 to 1000 ng/ml, preferably 1 to 100 ng/ml, more preferably 5 to 50 ng/ml, in particular 10 ng/ml.

The GDF5 in step (iii) includes GDF5 derived from an animal such as a human and a non-human animal and functionally modified derivatives thereof. The GDF5 may be, for example, a commercially available product produced by PeproTech etc. The concentration of GDF5 used in this step is 0.1 to 1000 ng/ml, preferably 1 to 100 ng/ml, more preferably 5 to 50 ng/ml, in particular 10 ng/ml.

The culture temperature in step (iii) is not particularly limited, but, for example, ranges from about 3° C. to about 40° C., and is preferably about 37° C. The culture is performed under an air atmosphere containing $CO_2$. The $CO_2$ concentration ranges from about 2% to 5%, and is preferably about 5%. The culture period in this step is, for example, 10 to 30 days, and is preferably 14 to 28 days.

(iv) Step of Further Culturing the Cells Obtained by Step (iii) in Suspension Culture Chondrocytes are obtained at the end of step (iii), but in order to obtain more mature chondrocytes, the cells obtained in the culture in step (iii) may be further cultured in suspension culture.

The medium used in step (iv) is a basal medium for animal cell culture. Examples of the basal medium include IMDM medium, Medium 199, Eagle's minimum essential medium (EMEM), αMEM medium, Dulbecco's modified Eagle's medium (DMEM), Ham's F12 medium, RPMI 1640 medium, Fischer's medium, and a mixed medium thereof. These media may contain serum (e.g., FBS) or no serum. If necessary, the media may contain one or more serum substitutes such as albumin, transferrin, KnockOut Serum Replacement (KSR) (serum substitute for FBS in ES cell culture) (Invitrogen), N2 supplement (Invitrogen), B27 supplement (Invitrogen), fatty acids, insulin, collagen progenitors, trace elements, 2-mercaptoethanol, and 3'-thiolglycerol, as well as one or more substances such as lipids, amino acids, L-glutamine, GlutaMAX (Invitrogen), nonessential amino acids (NEAAs), vitamins, growth factors, low-molecular-weight compounds, antibiotics, antioxidants, pyruvic acid, buffering agents, and inorganic salts. In one embodiment of this step, the basal medium is DMEM containing 10% serum.

The culture temperature in step (iv) is not particularly limited, but, for example, ranges from about 30° C. to about 40° C., and is preferably about 37° C. The culture is performed under an air atmosphere containing $CO_2$. The $CO_2$ concentration ranges from about 2% to 5%, and is preferably about 5%. A longer culture period in this step causes no problems on the production of chondrocytes, and hence the culture period is, for example, 20 days or more, and is preferably 28 days or more.

The present invention provides induced chondrocytes from pluripotent stem cells as described above. The induced chondrocytes have the following characteristics:
(1) the chondrocytes have at least 100-fold increase in COL2A1 gene expression compared with that in the pluripotent stem cells,
(2) the chondrocytes have at least 250-fold increase in SOX9 gene expression compared with that in the pluripotent stem cells, and
(3) the chondrocytes have no foreign gene introduced therein (except for foreign genes used for iPS cell production).

The expressions of COL2A1 and SOX9 genes herein are measured in terms of the mRNA levels per cell by a method well known to a person skilled in the art. Examples of the measurement method include RT-PCR, Northern blotting, etc. The measurement by PCR will be described in detail in Examples described later.

The increase in the expression level of the COL2A1 gene in the induced chondrocytes of the present invention compared with that in the pluripotent stem cells is preferably at least 50-fold or more, 100-fold or more, 150-fold or more, 200-fold or more, 250-fold or more, 260-fold or more, 270-fold or more, 280-fold or more, 290-fold or more, 300-fold or more, 400-fold or more, 500-fold or more, 600-fold or more, 700-fold or more, 800-fold or more, 900-fold or more, or 1000-fold or more. The increase is more preferably 280-fold or more.

The increase in the expression level of the SOX9 gene in the induced chondrocytes of the present invention compared with that in the pluripotent stem cells is preferably at least 50-fold or more, 100-fold or more, 150-fold or more, 200-fold or more, 250-fold or more, 260-fold or more, 270-fold or more, 280-fold or more, 290-fold or more, 300-fold or more, 400-fold or more, 500-fold or more, 600-fold or more, 700-fold or more, 800-fold or more, 900-fold or more, or 1000-fold or more. The increase is more preferably 500-fold or more.

The induced chondrocytes of the present invention can be cultured in the medium used in step (iv). The culture temperature and other conditions are the same as those in step (iv).

The present invention provides a cartilaginous tissue having three-dimensional structure produced by culturing the induced chondrocytes. The cartilaginous tissue is composed of an outer membrane and inner components surrounded by the outer membrane. The outer membrane comprises COL1 fibers but no COL2 fibers and has a thickness of 10 to 50 µm. The inner components comprise COL11 fibers, COL2 fibers, proteoglycans and the induced chondrocytes.

The cartilaginous tissue of the present invention is in the form of a spherical particle with a diameter of 0.5 mm to 5 mm. The spherical particles can be fused together, and hence the size is not particularly limited as long as the longest diameter is at least 0.5 mm or more.

The thickness of the outer membrane herein is not particularly limited as long as the cartilaginous tissue maintains adequate mechanical strength in a joint of a living body and can be integrated with the tissue of the recipient when transplanted into a joint of a living body. The thickness is, for example, 10 to 50 µm, 15 to 40 µm, or 20 to 30 µm. The thickness of the outer membrane can be measured as follows. Cartilaginous tissue sections are prepared and then stained with an anti-COL1 antibody, and the thickness of the stained part is measured on microscopic images. The section used for the measurement preferably has the largest cross-sectional area of the cartilaginous tissue. When the thickness of the outer membrane is not uniform in a cartilaginous tissue section, the largest thickness in the section can be taken as the thickness of the outer membrane.

The COL1 fibers herein are fibers having a triple helix structure formed by protein chains encoded by the COL1 gene.

The COL2 fibers herein are fibers having a triple helix structure formed by protein chains encoded by the COL2 gene.

The COL11 fibers herein are fibers having a triple helix structure formed by protein chains encoded by the COL11 gene.

The term "proteoglycans" herein refers to a group of compounds in which polysaccharides composed of repeating disaccharide units (such as chondroitin sulfate) are linked to amino acid (serine) residues on a core protein via saccharides (xylose, galactose and/or glucuronic acid).

The present invention provides a pharmaceutical product comprising the chondrocytes obtained by the method described above. The pharmaceutical product is administered to a patient, for example, as follows. The culture products (particles) composed of the chondrocytes obtained by the above method and an extracellular matrix from the chondrocytes are gathered with a fibrin glue to form a cluster with an appropriate size for the transplantation site. The gathered particles are transplanted into the defect site in the cartilage of a patient. Alternatively, the particles are mixed with gelatin gel, collagen gel and/or hyaluronic acid gel, etc., and transplanted into the defect site. Alternatively, the particles are transplanted into the defect site and fixed with the periosteum.

Examples of the diseases to be treated with the pharmaceutical product include defects in the cartilage in the face, such as nasal cartilage and conchal cartilage, and defects in the articular cartilage. The pharmaceutical product is preferably used for treatment of articular cartilage injury.

In the present invention, the number of the particles contained in the pharmaceutical product is not particularly limited as long as the number is sufficient for successful grafting of the transplant. The number of the particles may be reduced or increased as appropriate for the size of the defect site or the body size of the patient.

The present invention will be described more specifically with reference to Examples below, but the present invention is not limited thereto.

Examples

Human iPS Cells

The cell lines 409B2, HDF-11 and KF4009-1 were established from human dermal fibroblasts, and the cell line 604B1 was established from human peripheral blood cells, by the introduction of reprogramming factors using episomal vectors in accordance with Nature Methods 8, 409-412 (2011). These four human iPS cell lines were used in the experiments. The 409B2 cell line (Nat Methods. 8, 409-412 (2011)) and the 604B1 cell line (Stem Cells. 31, 458-466 (2013)) were gifts from Center for iPS Cell Research and Application, Kyoto University. The established iPS cell lines were reseeded on feeder cells (mitomycin-C-treated SNL cells), then human ES cell maintenance medium was added, and the cell lines were cultured for maintenance. The human ES cell maintenance medium was prepared by mixing DMEM/F12 (Sigma) with 20% KSR (Invitrogen), 2 mM L-glutamine (Invitrogen), $1\times10^{-4}$ M nonessential amino acids (Invitrogen), $1\times10^{-4}$ M 2-mercaptoethanol (Invitrogen), 50 units/ml penicillin (Invitrogen), 50 mg/ml streptomycin (Invitrogen), and 4 ng/ml bFGF (WAKO). The iPS cell lines were transferred to Matrigel (Invitrogen)-coated dishes, then Essential 8 medium (Life Technologies) supplemented with 50 units/ml penicillin and 50 mg/ml streptomycin was added, and the cell lines were cultured for maintenance in the feeder-free environment. The iPS cell lines formed colonies that consisted of 1 to $2\times10^5$ cells 10 to 15 days after the start of maintenance under the feeder-free culture conditions. The colonies were subjected to differentiation into chondrocytes as described below.

Isolation of RNAs and Quantitative Real-Time RT-PCR

RNAs for RT-PCR were collected from the desired cells using RNeasy Mini Kit (Qiagen) with DNase I digestion in the column in accordance with the manufacturer's protocol. In cases where RNAs were collected from the cells in particles, the particles were homogenized using a mortar and then subjected to RNA collection. To prepare templates, 500 ng of the total RNAs were converted to cDNAs using ReverTra Ace (TOYOBO). Real-time PCR was performed on Step One system (ABI) using KAPA SYBR FAST qPCR kit Master Mix ABI prism (KAPA BIOSYSTEMS). The primers used for the PCR are shown below.

| Primer | Sequence |
|---|---|
| ACTB F | TGGCACCACACCTTCTACAATGAGC (SEQ ID NO: 1) |
| ACTB R | GCACAGCTTCTCCTTAATGTCACGC (SEQ ID NO: 2) |
| OCT3/4 | FGACAACAATGAGAACCTTCA (SEQ ID NO: 3) |
| OCT3/4 R | TTCTGGCGCCGGTTACAGAA (SEQ ID NO: 4) |
| NANOG F | CAAAGGCAAACAACCCACTT (SEQ ID NO: 5) |
| NANOG R | CTGGATGTTCTGGGTCTGGT (SEQ ID NO: 6) |
| BRACHYURY F | TATGAGCCTCGAATCCACATAGT (SEQ ID NO: 7) |
| BRACHYURY R | CCTCGTTCTGATAAGCAGTCAC (SEQ ID NO: 8) |
| KDR F | GGCCCAATAATCAGAGTGGCA (SEQ ID NO: 9) |
| KDR R | CCAGTGTCATTTCCGATCACTTT (SEQ ID NO: 10) |
| SOX5 F | CAGCCAGAGTTACACAATAGG (SEQ ID NO: 11) |
| SOX5 R | CTGTTGTTCCCGTCGGAGTT (SEQ ID NO: 12) |
| SOX6 F | GGATGCAATGACCCAGGATTT (SEQ ID NO: 13) |
| SOX6 R | TGAATGGTACTGACAAGTGTTGG (SEQ ID NO: 14) |
| SOX9 F | AGACCTTTGGGCTGCCTTAT (SEQ ID NO: 15) |
| SOX9 R | TAGCCTCCCTCACTCCAAGA (SEQ ID NO: 16) |
| AGGRECAN F | TGAGGAGGGCTGGAACAAGTACC (SEQ ID NO: 17) |
| AGGRECAN R | GGAGGTGGTAATTGCAGGGAACA (SEQ ID NO: 18) |
| COL2A1 F | TTTCCCAGGTCAAGATGGTC (SEQ ID NO: 19) |
| COL2A1 R | CTTCAGCACCTGTCTCACCA (SEQ ID NO: 20) |
| COL11A2 F | TGTGATGACTACGGGGACAA (SEQ ID NO: 21) |
| COL11A2 R | CCATATTCCTCTGCCTGGAA (SEQ ID NO: 22) |
| LUBRICIN F | AAAGTCAGCACATCTCCCAAG (SEQ ID NO: 23) |
| LUBRICIN R | GTGTCTCTTTAGCGGAAGTAGTC (SEQ ID NO: 24) |
| IHH F | AACTCGCTGGCTATCTCGGT (SEQ ID NO: 25) |
| IHH R | GCCCTCATAATGCAGGGACT (SEQ ID NO: 26) |
| COL10A1 F | ATGCTGCCACAAAATACCCTTT (SEQ ID NO: 27) |
| COL10A1 F | GGTAGTGGGCCTTTTATGCCT (SEQ ID NO: 28) |
| COL1A1 F | GTCGAGGGCCAAGACGAAG (SEQ ID NO: 29) |
| COL1A1 R | CAGATCACGTCATCGCACAAC (SEQ ID NO: 30) |
| COL1A2 F | AATTGGAGCTGTTGGTAACGC (SEQ ID NO: 31) |
| COL1A2 R | CACCAGTAAGGCCGTTTGC (SEQ ID NO: 32) |

| Primer | Sequence |
|---|---|
| OSTEOCALICN F | CACTCCTCGCCCTATTGGC (SEQ ID NO: 33) |
| OSTEOCALCIN R | CCCTCCTGCTTGGACACAAAG (SEQ ID NO: 34) |
| Taqman human ACTB | Hs01060665-g1 |
| Taqman human Actb | Mn00607939-s1 |
| Taqman rat Actb | Rn00667869-m1 |
| eGFP COL11A2 F | CATACAATGGGGTACCTTCTGG (SEQ ID NO: 35) |
| eGFP COL11A2 R | GCATGGACGAGCTGTACAAGTAA (SEQ ID NO: 36) |

Generation of iPS Cells that Express GFP in a Chondrocyte-Specific Manner

Figure 2:
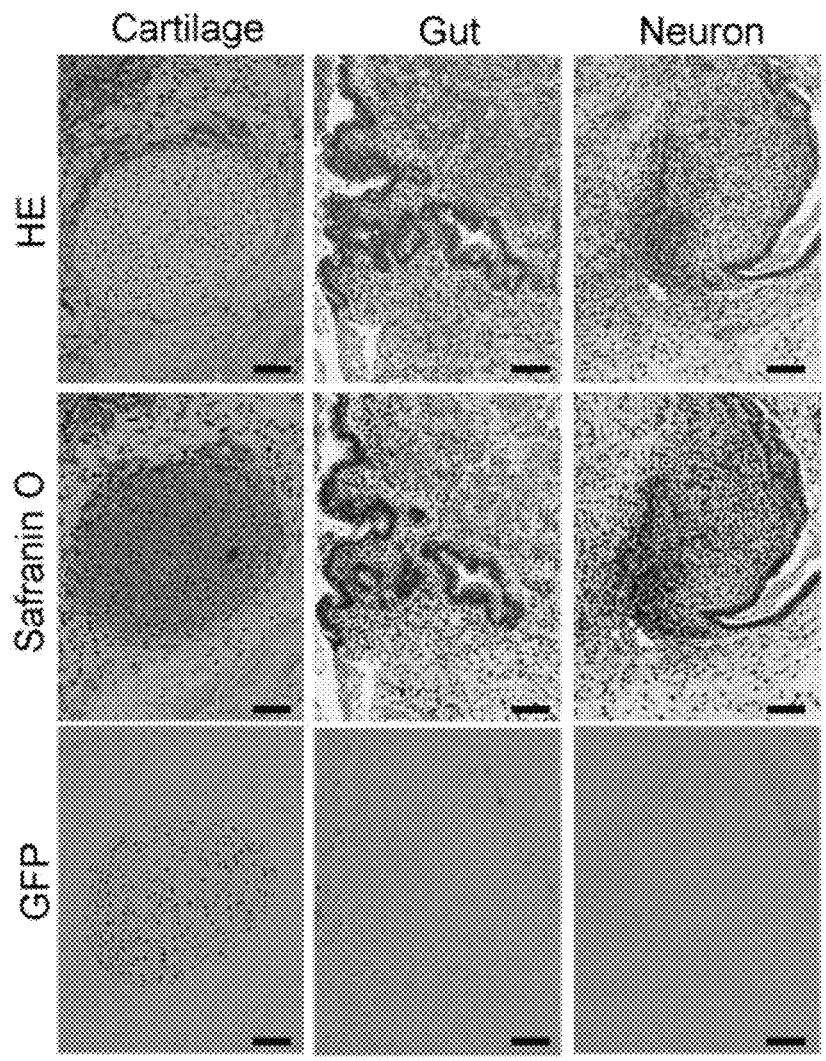
FIG. 2 shows the histological staining of the teratomas harvested from SCID mice subcutaneously injected with the Col11a2 gene reporter iPS cells generated by introducing Col11a2-EGFP-IRES-Puro into iPS cell lines.

The piggyBac vector carrying a transgene construct linked to the promoter and enhancer of the chondrocyte-specific Col11a2 gene (the type XI collagen a2 chain gene) (Col11a2-EGFP-IRES-Puro, see FIG. 1) was introduced into human iPS cells. Ten days after introduction, reporter iPS cell lines that expressed green fluorescent protein (GFP) in a Col11a2 gene specific manner were selected. Incorporation of the reporter gene to the selected iPS cell lines were identified by RT-PCR. The selected Col11a2 gene reporter iPS cell lines were subcutaneously injected into SCID mice, which formed teratomas. The teratomas were harvested and subjected to histological staining. The formation of cartilage, gut, and nervous tissue was observed, and the chondrocyte-specific expression was also observed (FIG. 2).

Optimization of Induction of Differentiation Toward Chondrocytes

Ten to fifteen days after the start of maintenance culture under feeder-free conditions, the medium of the Col11a2 gene reporter iPS cells were exchanged with mesodermal medium (prepared by mixing DMEM/F12 with 10 ng/ml Wnt3A (R&D), 10 ng/ml Activin A (R&D), 1% insulin-transferrin-sodium selenite (Invitrogen), 1% fetal calf serum, 50 units/ml penicillin, and 50 mg/ml streptomycin). After three days of culture (day 3), one of the chondrogenic supplements with the formula (1) to (3) shown below was added to DMEM/F12 supplemented with 1% insulin-transferrin-sodium selenite, 1% FBS, 50 units/ml penicillin, and 50 mg/ml streptomycin. The cells were cultured until day 14 from the start of the differentiation induction. The 14-day culture process was performed by adherent culture. During day 3 to day 14, 10 ng/ml bFGF was added to promote the growth.

(1) A: 50 µg/ml ascorbic acid (Nakarai).
(2) ABT: mixed solution of 50 µg/ml ascorbic acid, 10 ng/ml BMP2 (Osteopharma) and 10 ng/ml TGFβ (PeproTech).
(3) ABTG: 50 µg/ml ascorbic acid, 10 ng/ml BMP2 (Osteopharma), 10 ng/ml TGFβ (PeproTech) and 10 ng/ml GDF5.

Figure 4A:
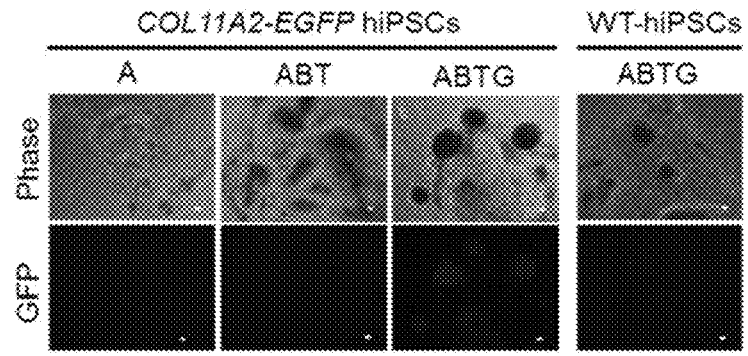
FIG. 4A shows the phase-contrast microscopy images (top panels) and the fluorescent microscopy images (bottom panels) of the Col11a2 gene reporter iPS cell-derived cells and the wild-type iPS cell-derived cells on day 14 after induction under each of the conditions (A, ABT or ABTG).

The cultures were examined under a phase-contrast microscope on day 14 (FIG. 4A). The formation of cell nodules with multilayered cell structure was observed in the cell differentiation cultures supplemented with ABT and ABTG, but no nodule formation was observed in the culture supplemented with the above (1) containing ascorbic acid alone.

The terms "day 0", "day 3", "day 10", "day 14", "day 15", "day 21", "day 28", "day 42", "day 52", "day 56", "day 70" and "day 140" as used herein to indicate the culture period for the differentiation induction step mean "the start of the differentiation induction", "day 3 after the start of the differentiation induction", "day 10 after the start of the differentiation induction", "day 14 after the start of the differentiation induction", "day 15 after the start of the differentiation induction", "day 21 after the start of the differentiation induction", "day 28 after the start of the differentiation induction", "day 42 after the start of the differentiation induction", "day 52 after the start of the differentiation induction", "day 56 after the start of the differentiation induction", "day 70 after the start of the differentiation induction", and "day 140 after the start of the differentiation induction", respectively.

Figure 4B:
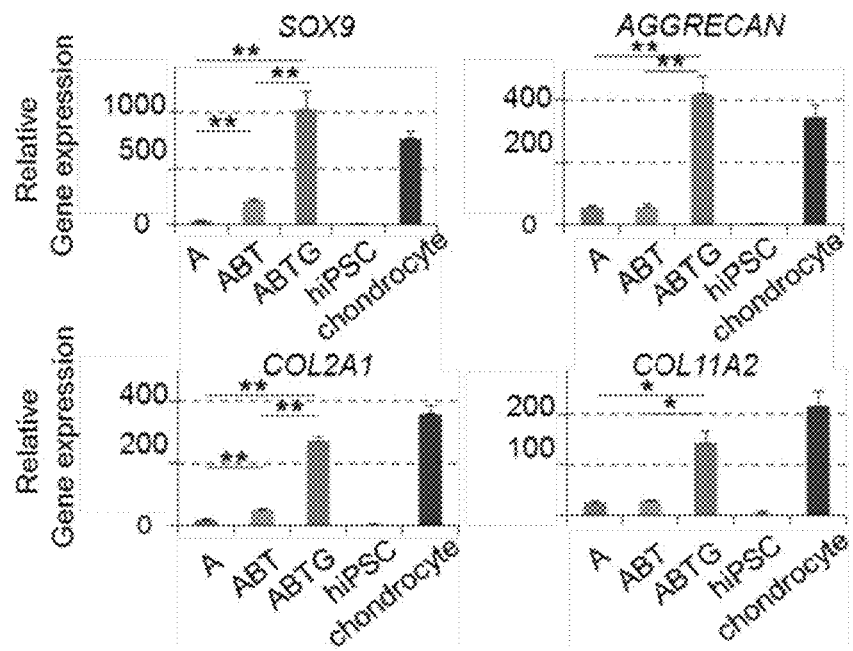
FIG. 4B shows the results of RT-PCR analysis of the expressions of SOX9, AGGRECAN, COL2A1 and COL11A2 in the Col11a2 gene reporter iPS cell-derived cells on day 28 after induction under each of the conditions (A, ABT or ABTG). The term "Chondrocyte" in the figure indicates human chondrocytes (402RD-R10f) purchased from Cell Applications, Inc. used as a positive control.
Figure 4C:
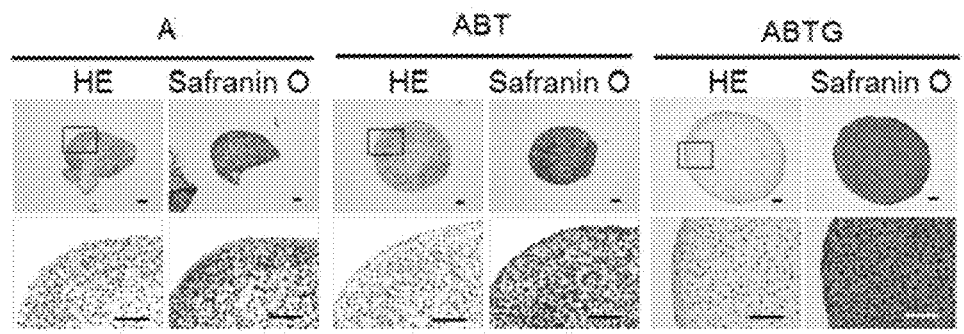
FIG. 4C shows the HE and safranin O staining of the cells on day 42 after induction under each of the conditions (A, ABT or ABTG).

On day 14 after the start of the differentiation induction, the cell nodules were separated from the dishes by pipetting, transferred to petri dishes, and suspension culture was performed in the same medium. The cell nodules were easily separated due to the decrease in the adhesion ability by the action of the chondrocyte extracellular matrix (ECM). The medium was changed every 2 to 7 days. RNAs were extracted from the particles on day 28 after the start of the differentiation induction, and subjected to real-time PCR analysis of the expressions of chondrocyte marker genes (FIG. 4B). The effectiveness of the chondrogenic medium supplemented with ABTG in inducing chondrocytes was confirmed by significantly high expression levels of chondrocyte marker genes. The particles were stained with safranin O for staining cartilage matrix on day 42 after the start of the differentiation induction and examined under an optical microscope (FIG. 4C). The most intense staining with safranin O was observed in the cell particles cultured in the ABTG-supplemented medium.

The above results revealed that the ABTG-supplemented medium most efficiently produced chondrocytes in the adherent culture step on day 3 to day 14 and the suspension culture step on day 14 to day 42. Based on this, ABTG supplementation was used in the subsequent experiments.

The same protocol performed showed that chondrocytes could also be generated from other human iPS cell lines (409B2, HDF-11, KF4009-1 and 604B1 cell lines) (day 42).

Figure 5:
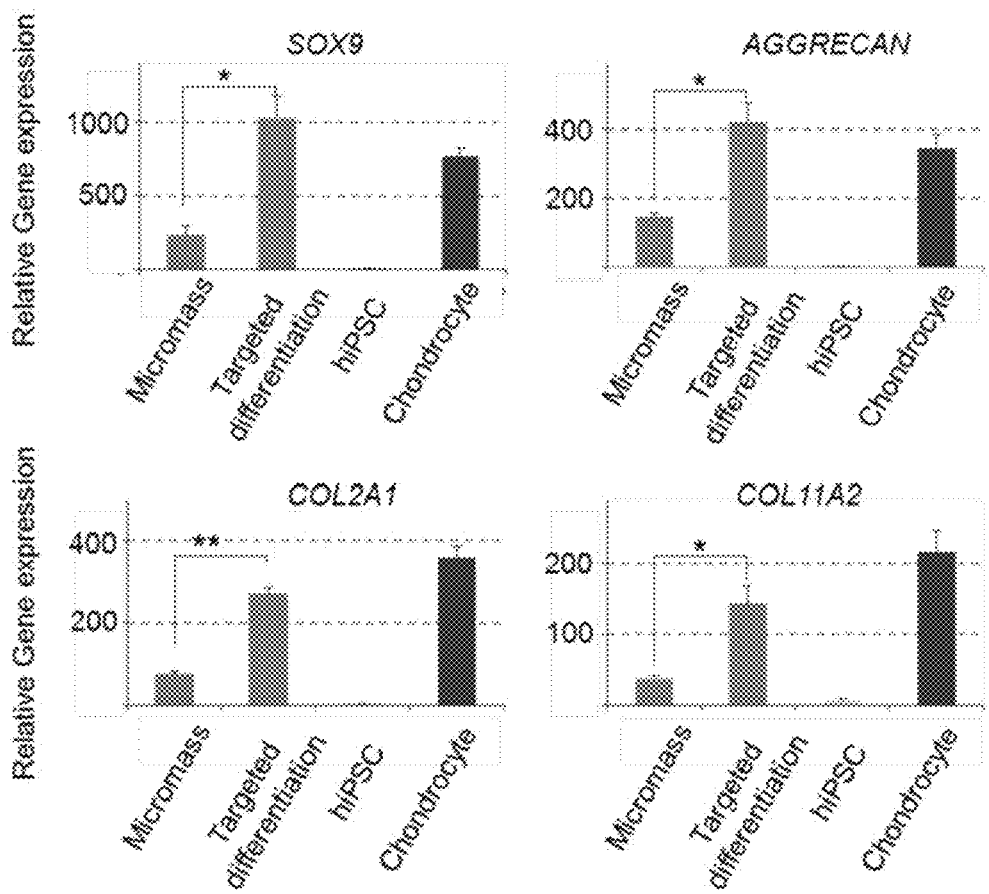
FIG. 5 shows the results of RT-PCR analysis of the expressions of SOX9, AGGRECAN, COL2A1 and COL11A2 in the cells on day 28 after induction by the conventional method (micromass) or by the protocol of the present invention.
Figure 6A:
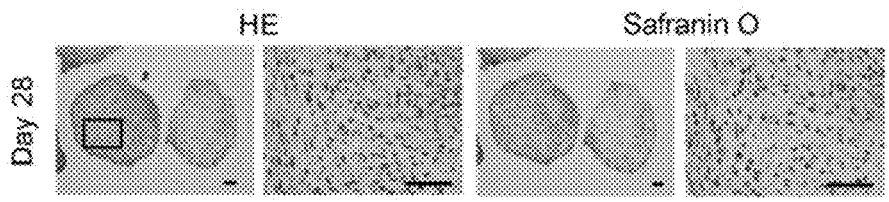
FIG. 6A shows the HE and safranin O staining of the particles on day 28 after induction by the protocol of the present invention.
Figure 6B:
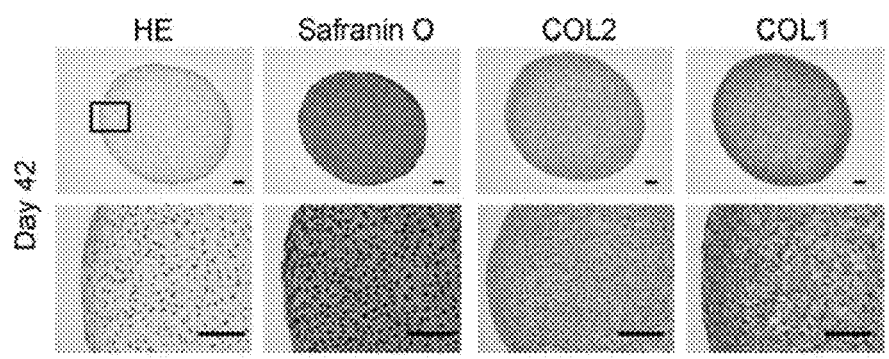
FIG. 6B shows the HE and safranin O staining and types II and I collagen staining of the particles on day 42 after induction by the protocol of the present invention.
Figure 6C:
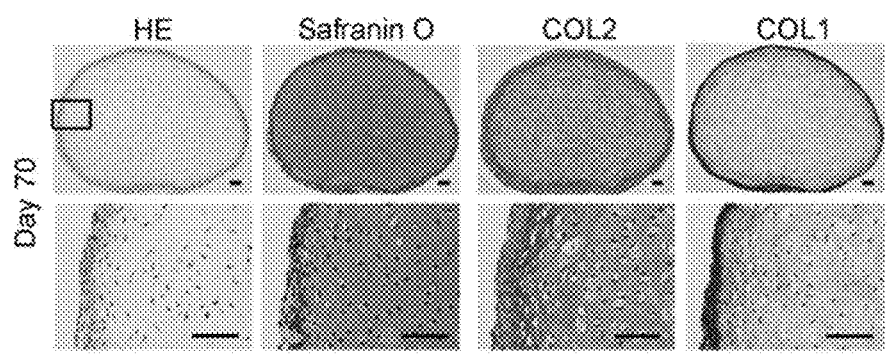
FIG. 6C shows the HE and safranin O staining and types II and I collagen staining of the particles on day 70 after induction by the protocol of the present invention (the medium was replaced with serum-supplemented medium on day 42).
Figure 6D:
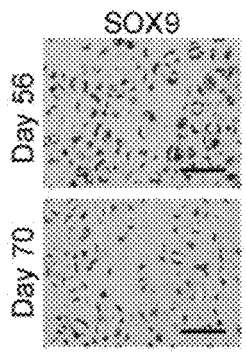
FIG. 6D shows the SOX9 staining of the particles on days 56 and 70 after induction by the protocol of the present invention (the medium was replaced with serum-supplemented medium on day 42).
Figure 6E:
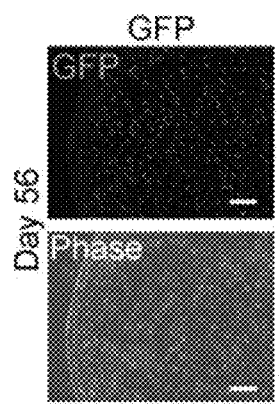
FIG. 6E shows the fluorescent microscopy images of GFP in the particles on day 56 after induction by the protocol of the present invention (the medium was replaced with serum-supplemented medium on day 42).
Figure 6F:
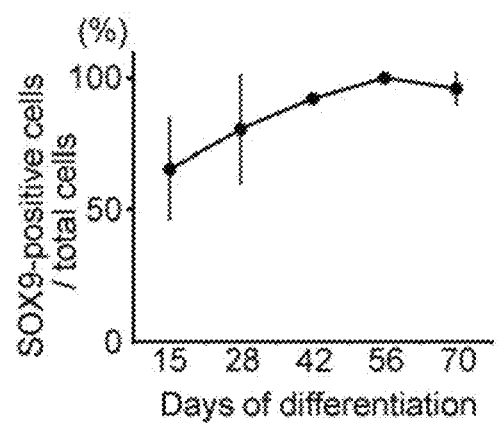
FIG. 6F shows the time course of the ratio of the number of SOX9-positive cells per total cells induced by the protocol of the present invention (the medium was replaced with serum-supplemented medium on day 42).

Two types of chondrocytes were generated either by the conventional suspension culture (micromass formation) for chondrogenic induction (Sci Rep. 3, 1978 (2013)) or the protocol of the present invention involving the mesoderm induction on day 0 to day 3 of culture (adherent culture in a medium supplemented with Wnt3A and Activin A). The RT-PCR analysis of chondrocyte marker genes for comparison of the chondrocytes showed that significantly higher expressions of the marker genes in the protocol of the present invention involving the mesoderm induction (FIG. 5). These results revealed that the mesoderm induction from iPS cells is useful for chondrogenic induction.

Analysis of Particles

Figure 3:
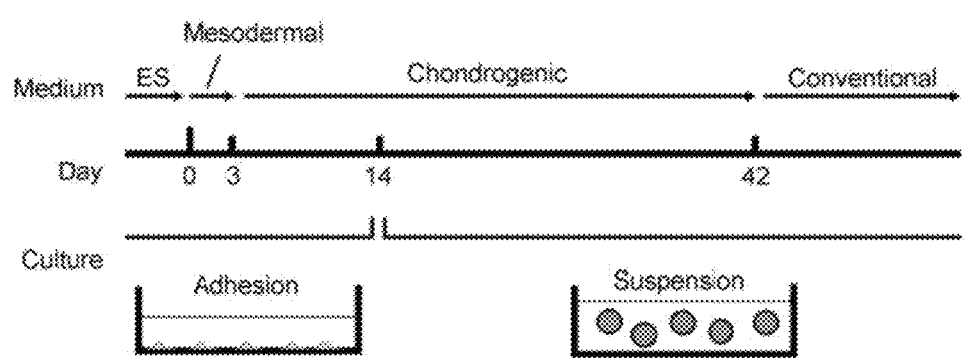
FIG. 3 shows a schematic representation of the protocol for inducing chondrocytes from pluripotent stem cells.
Figure 7A:
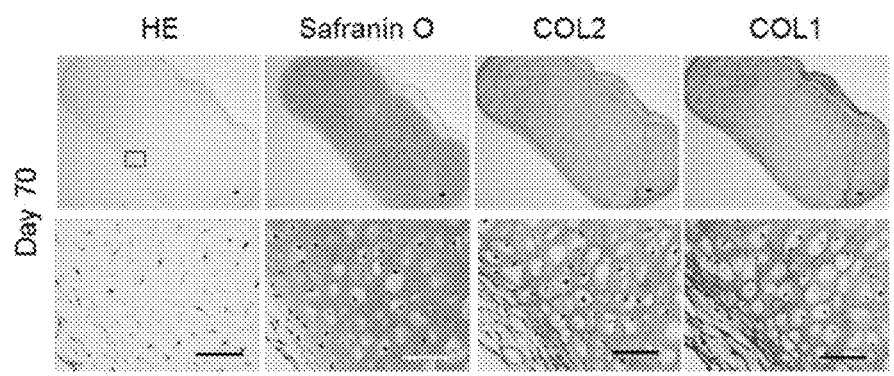
FIG. 7A shows the HE and safranin O staining and types II and I collagen staining of the particles on day 70 after induction by a modified protocol of the present invention in which the nodules were continuously cultured in chondrogenic medium, without medium replacement with serum-supplemented medium on day 42.
Figure 7B:
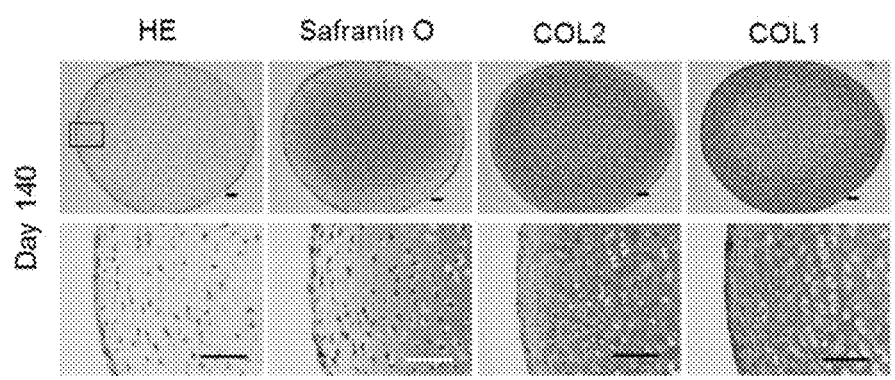
FIG. 7B shows the HE and safranin O staining and types II and I collagen staining of the particles on day 140 after induction by a modified protocol of the present invention in which the nodules were continuously cultured in chondrogenic medium, without medium replacement with serum-supplemented medium on day 42.

The iPS cells were subjected to induction by the cell differentiation culture protocol as represented in FIG. 3, and the particles were examined by histological staining on days 28, 42, 70 and 140 (FIG. 6). The chondrogenic medium used on days 3 to 42 was DMEM/F12 supplemented with 1% insulin-transferrin-sodium selenite, 1% fetal calf serum, 50 units/ml penicillin, 50 mg/ml streptomycin and ABTG. The results indicated that the particles on day 28 were surrounded by ECM stained slightly with safranin 0 (FIG. 6A). The ECM in the particles matured, as indicated by intense staining with safranin O on day 42. However, the ECM contained both types I and II collagen. The culture was continued in the chondrogenic medium used on day 42, and the particles maintained the expression of type I collagen on day 70 or 140 (FIGS. 7A and 7B). However, the replacement of the chondrogenic medium to conventional DMEM medium with 10% fetal calf serum on day 42 and subsequent culture resulted in decreased type I collagen expression and increased type II collagen expression on day 70 (FIGS. 6B and 6C). Type X collagen expression was below the detection limit. The surface membrane of the particles showed increased type I collagen expression. Such changes were not observed in the culture continued in the chondrogenic medium. It was speculated that the surface membrane contributed to the induction of the hyaline-cartilaginous maturation inside the particles. The number of SOX9-positive cells in the particles were counted, except for those in the surface membrane, using the chondrocyte-specific expression indicator SOX9 on days 56 and 70 (FIG. 6D). The density of chondrocytes in the particles gradually increased with time, reaching 91.8%±0.91% on day 56 and 99.7%±0.2% on day 70 (FIG. 6F). Almost all cells expressed COL11A2-EGFP on day 56 (FIG. 6E). The results indicated that the three-dimensional structure of the particles was important and effective at inducing the hyaline-cartilaginous maturation of chondrocytes in continuous culture without the chondrogenic medium.

Effects of Suspension Culture

Figure 8:
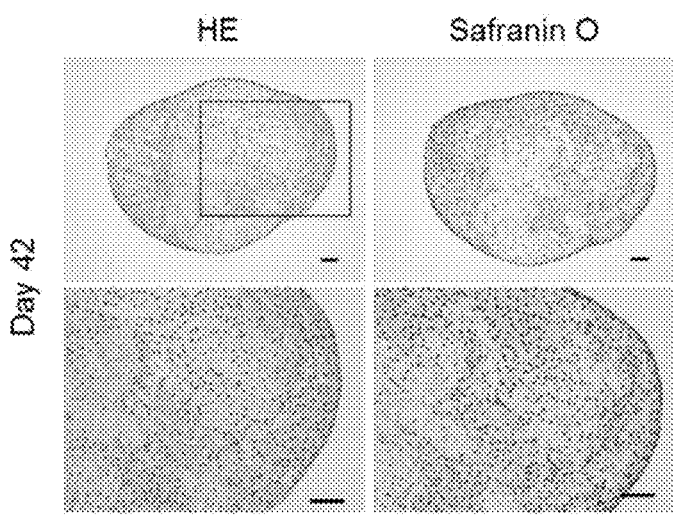
FIG. 8 shows the HE and safranin O staining of the particles on day 42 after induction by a modified protocol of the present invention in which adherent culture was continued beyond day 14 until day 42.
Figure 9A:
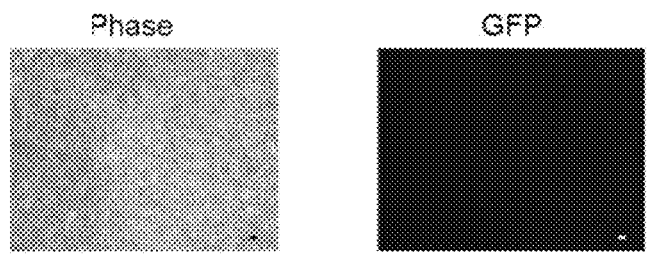
FIG. 9A shows the phase-contrast microscopy image (left panel) and the fluorescent microscopy image (right panel) of the cells attached on the dish bottoms on day 42.
Figure 9B:
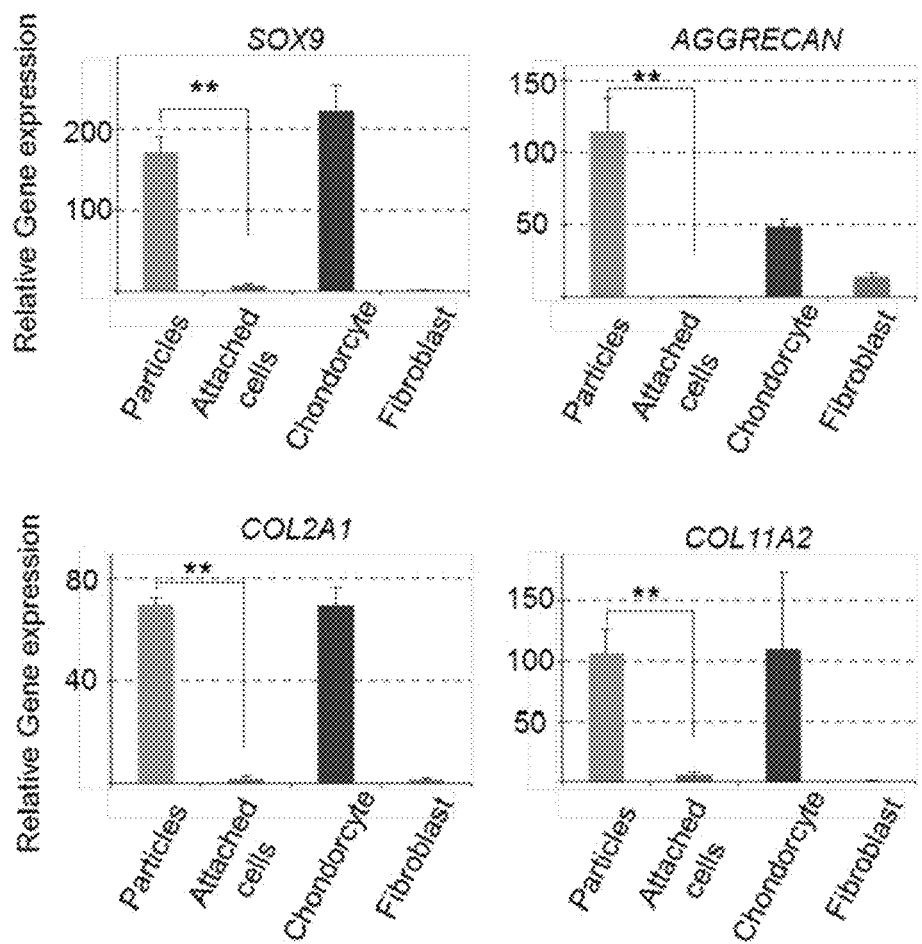
FIG. 9B shows the results of RT-PCR analysis of the expressions of SOX9, AGGRECAN, COL2A1 and COL11A2 in the particles and the dish bottom-attached cells on day 42 after induction by the protocol of the present invention. The RNA expression levels of the genes were normalized to the expression level of β-activin (as indicated by ACTB). The controls were redifferentiated chondrocytes (as indicated by Chondrocyte) and fibroblasts (as indicated by Fibroblast).

Suspension culture was performed after day 14 according to the protocol of the present invention. Separately, adherent culture was continued beyond day 14, and poor cartilage formation was observed on day 42 (FIG. 8). The results identified that suspension culture facilitates cartilaginous maturation. After transferring the cells to suspension culture in new dishes on day 14, the dish bottoms became covered with cells. These cells attached on the dish bottoms had a spindle-shaped morphology and did not exhibit COL11A2-EGFP (FIG. 9A). The RT-PCR analysis of the cells showed very low level of expressions of chondrocyte marker genes (FIG. 9B). These results suggest that the cells other than chondrocytes of interest attached to the dish bottoms during the suspension culture, and in this manner, suspension culture enriched the chondrocytes.

Time-Course Analysis of Induction of Chondrogenic Differentiation

Figure 10A:
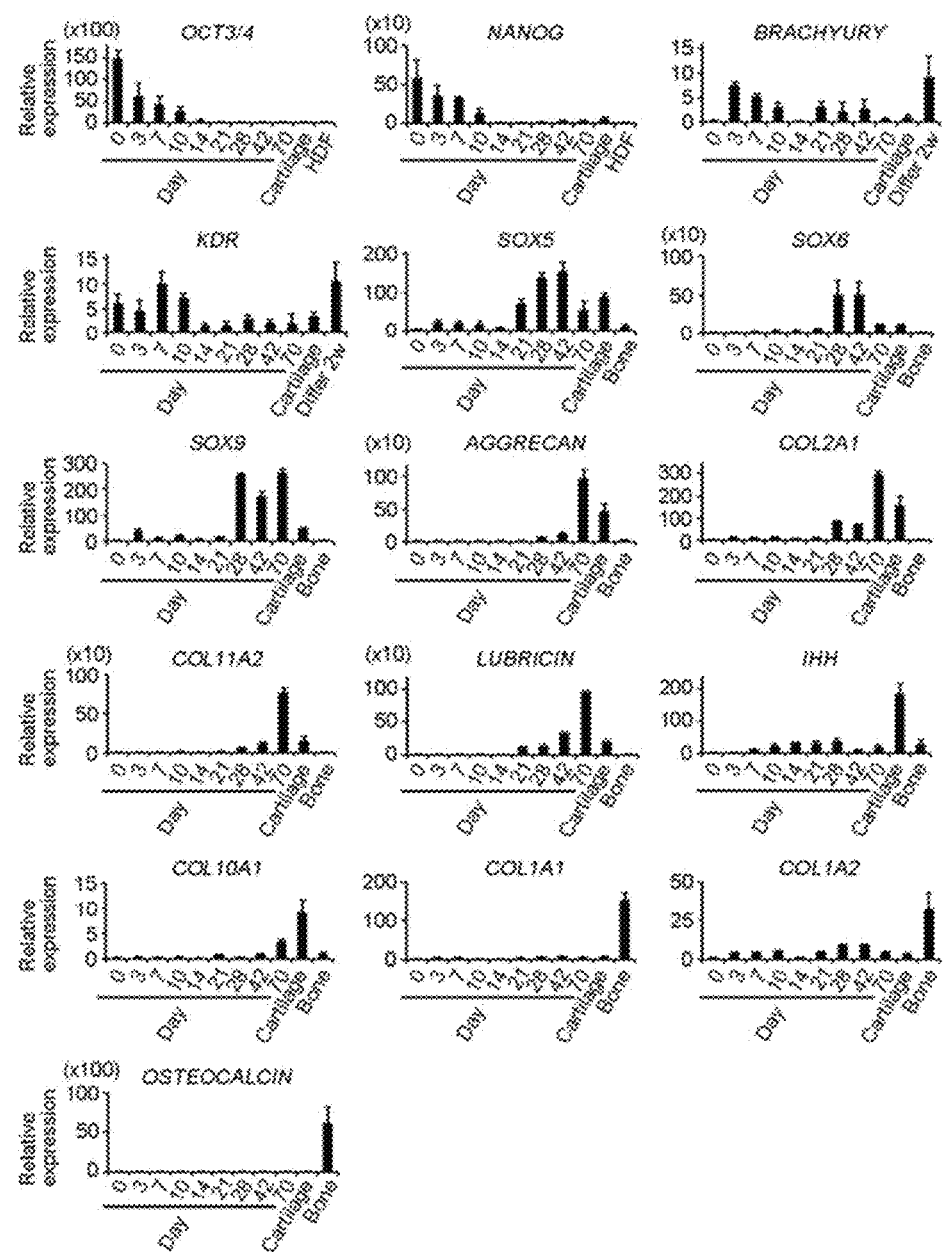
FIG. 10A shows the results of RT-PCR analysis of the genes in chondrocytes induced by the protocol of the present invention (from day 0 to day 70), human chondrocytes (as indicated by Cartilage) and chondrocytes induced by the conventional method (as indicated by Differ 2W, HDF, or Bone). The RNA expression levels of the genes were normalized to the level of β-activin (ACTB) expression. The controls were HDF, the cells at the second week of the differentiation, normal articular chondrocytes, and normal bone cells. The values were the mean values of n=3.

The protocol of the present invention mimics the developmental path way from the mesoderm to chondrocytes in living bodies, not using chondrogenic medium from the beginning of cell differentiation culture, and in this protocol, mesodermal medium was used instead of chondrogenic medium on day 0 to day 3. At the time of medium exchange, time-course analysis of the cells was performed at various intervals from the start of the differentiation induction using pluripotent markers, mesoderm markers and chondrocyte markers to examine the changes of the human iPS cells during differentiation culture. The analysis results are shown in FIG. 10A.

After the analysis on day 0, the addition of Wnt3a and Activin A in mesodermal medium decreased the expressions of pluripotent markers and transiently increased the expression of a marker specific to early stage mesoderm, BRACHYURY, in the cells on day 3. After switching the mesodermal medium to chondrogenic medium on day 3, the expressions of pluripotent markers further decreased from days 7 through 14, while the expression level of a marker specific to mesoderm, KDR, transiently increased on day 7. Culture of the particles were further continued, and the expression levels of markers specific to chondrocytes or the extracellular matrix, such as AGGRECAN, COL2A1 and LUBRICIN, exceeded the expression levels in articular cartilage as a positive control. Unlike articular cartilage as a positive control, the expressions of cartilage hypertrophy markers, IHH and COL10A1, were very low.

Figure 10B:
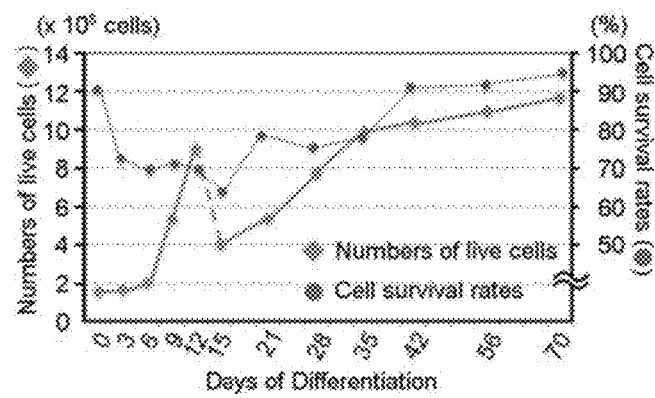
FIG. 10B shows the chart of live cell numbers (diamond symbols) and cell survival rates (circle symbols) at various intervals (from day 0 to day 70) after induction by the protocol of the present invention.

The live cell numbers were counted at various intervals and the time course was analyzed (FIG. 10B). The live cell numbers were counted by trypan blue staining. The lack of increase in the number of cells despite cell division by culturing and the reduced cell survival observed on days 0 to 3 suggest that non-mesodermal cells preferentially died under these conditions, contributing to the formation of a mesodermal-cell-rich population. The number of cells increased until day 14. On day 14, the cells in adherent culture were transferred to suspension culture. In this Example, only the number of cells in the particles floating in the culture was counted, which resulted in the decrease in the cell numbers on day 14. At the end of all the culture steps, the number of live cells was about seven times the total number of human iPS cells on day 0. On average, the number of human iPS cells on day 0 was $1.6\pm0.1\times10^5$ per 35-mm dish, and the number of cells survived on day 14 was $9.0\pm0.72\times10^5$ per 35-mm dish. Among these cells, $4.06\pm0.04\times10^5$ cells, on average, participated in the formation of the particles. The number of cells in the particles increased to $10.4\pm0.2\times10^5$ on day 42.

The average number of particles was 14.6±3.96 per dish. The average diameter of the particles was 0.69±0.2 mm on day 21, 0.8±0.16 mm on day 28, 1.13±0.18 mm on day 42, and 1.4±0.47 mm on day 70.

The amount of FBS used in this protocol was the minimum amount that provides the essential amount of growth factors required for chondrocyte survival. The non-chondrocytic cells might die under these conditions and drop out from the particles. As a result of the accumulation of non-chondrocytic cells on the dish bottoms and the harvest of floating particles, pure chondrocytes are successfully obtained without the use of cell sorting. Chondrocytes are lubricious and easily separated from the bottom of the dishes to be transferred from adherent culture to suspension culture. On the other hand, non-chondrocytic cells strongly adhere to the dish bottoms. Due to the difference in adhesive strength, pure chondrocytes are successfully separated from non-chondrocytic cells.

Assessment of Tumor Formation in Mice

Figure 11A:
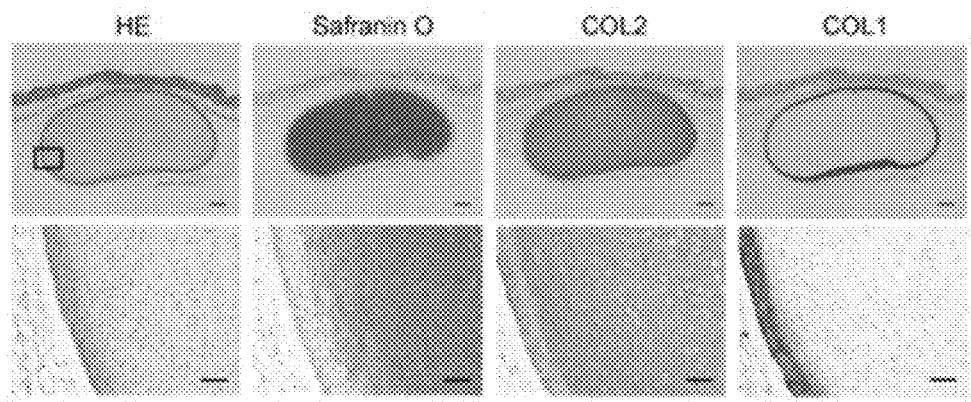
FIG. 11A shows the HE and safranin O staining and types II and I collagen staining of day-42 particles 12 weeks after transplantation into the subcutaneous space of SCID mice following particle induction by the protocol of the present invention.
Figure 11B:
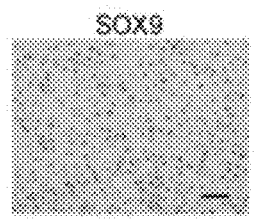
FIG. 11B shows the SOX9 staining of day-42 particle 12 weeks after transplantation into the subcutaneous space of SCID mice following particle induction by the protocol of the present invention.
Figure 11C:
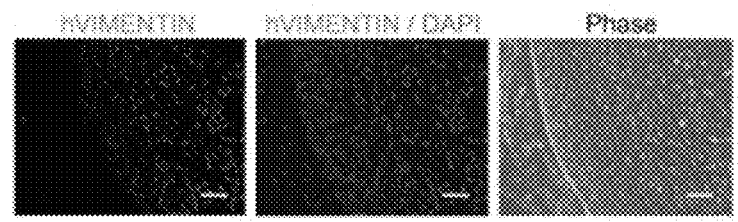
FIG. 11C shows the human vimentin staining and DAPI staining and phase-contrast microscopy image of day-42 particles 12 weeks after transplantation into the subcutaneous space of SCID mice following particle induction by the protocol of the present invention.

For analysis of the in vivo activity of the human iPS cell-derived chondrocytes produced as above, the day-42 chondrocytes were injected into the subcutaneous space of SCID mice. A histochemical analysis 12 weeks after injection revealed the formation of cartilaginous tissues in four out of six injection sites (FIG. 11A). The ratio of SOX9-positive cells in these cartilaginous tissues was 96.4±0.84% (FIG. 11B). The cartilaginous tissues appeared to have hyaline cartilage formation as indicated by SOX9 expression were surrounded by the surface membrane that expressed type I collagen. Immunostaining using non-human-derived vimentin antibodies showed that the hyaline cartilage of the subcutaneously formed tissues was human iPS cell derived, whereas the surrounding membrane was derived from the mice (FIG. 11C). There were no tumor formation or tissue alterations indicating tumor formation in any of the chondrocyte-transplanted sites. These results suggest that human iPS cell-derived chondrocytes have the ability to form and maintain hyaline cartilage in vivo for at least 12 weeks.

Figure 11D:
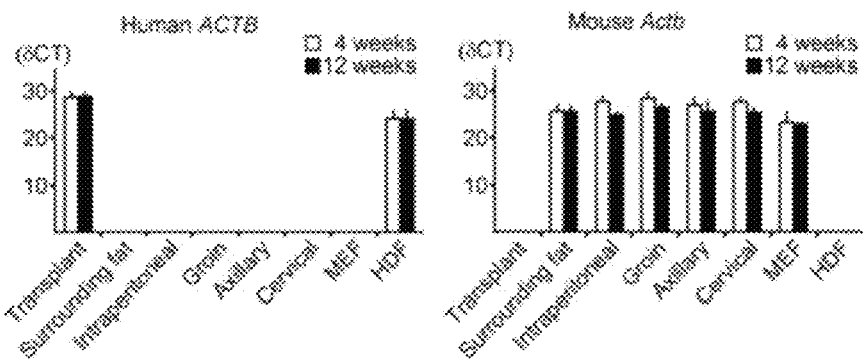
FIG. 11D shows the results of RT-PCR analysis of the expressions of human β-activin (ACTB) and mouse β-activin (Actb) in tissues 4 or 12 weeks after transplantation of day-42 particles into the subcutaneous space of SCID mice following particle induction by the protocol of the present invention.

No human β-actin mRNA was detected in the tissues and lymph nodes of the SCID mice, including cervix, peritoneal cavity, axillary lymph nodes, groin lymph nodes. The results deny the possibility of metastasis formation (FIG. 11D). The results suggest that the day-42 particles of the human iPS cell-derived chondrocytes are suitable for transplantation.

Long-Term Assessment In Vivo

Figure 12:
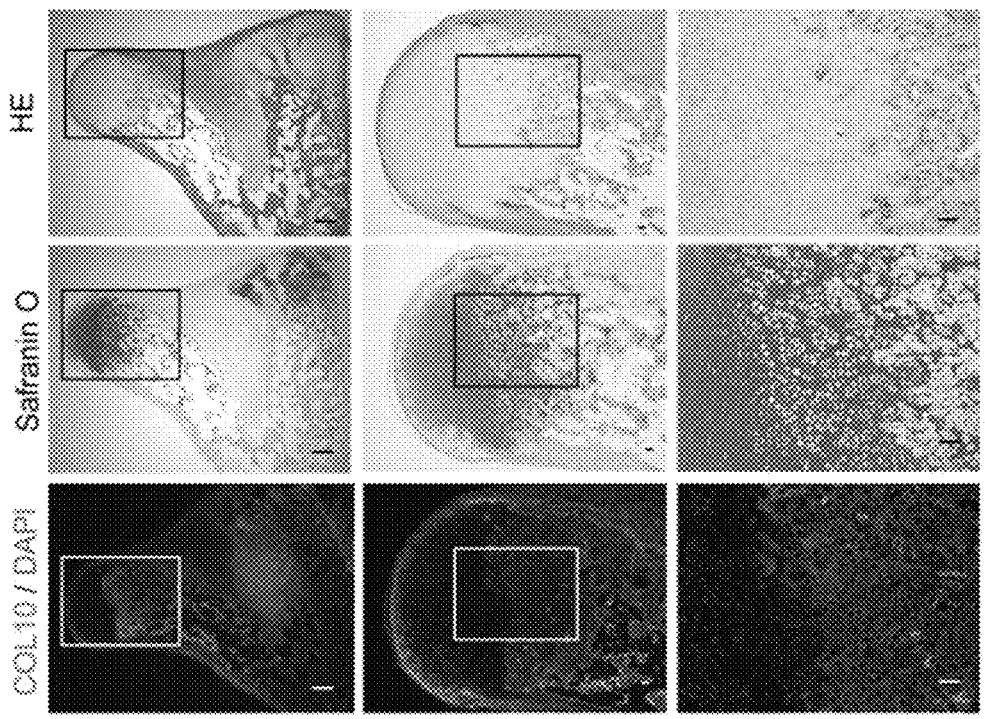
FIG. 12 shows the HE staining (top panels), safranin O staining (middle panels) and immunostaining with anti-type X collagen antibodies (bottom panels) in tissues after subcutaneous transplantation of iPS cell-derived cells. Magnified images of the boxed regions are shown in the panels to the right. Scale bars are 500 mm in the left panels and 50 mm in the middle and right panels.

Day-42 chondrocytes were injected into the subcutaneous space of SCID mice in the same manner as above, the transplanted sites were harvested 12 months after transplantation, and the harvested sites were subjected to histochemical analysis. All six samples showed partial cartilage hypertrophy, as indicated by the expression of type X collagen (FIG. 12). Among these samples, five had portions of the cartilage replaced with bone-like tissue, but a substantial amount of cartilage with a morphology resembling epiphyseal cartilage remained. These results suggest that the human iPS-derived cells obtained by the method of the present invention undergo hypertrophy, although at a very slow rate. This raises the possibility that transplantation into articular cartilage defects induce endochondral ossification. There were no signs of teratoma or other tumor formation at any of the transplanted sites even 12 months after transplantation.

Transplantation of Human iPS Cell-Derived Chondrocytes

Figure 13A:
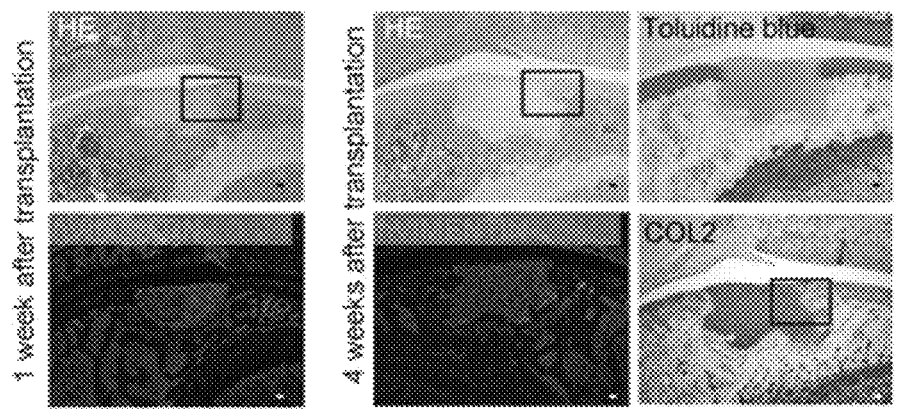
FIG. 13A shows the HE staining, human vimentin immunostaining, toluidine blue staining, and type II collagen immunostaining one week after (left panels) or four weeks after (right panels) transplantation of day-28 particles into the joints of SCID rats following particle induction by the protocol of the present invention.
Figure 13B:
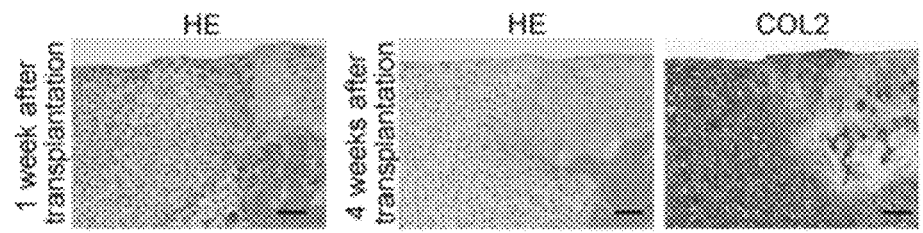
FIG. 13B shows the HE staining and type II collagen immunostaining one week after (left panel) or four weeks after (right panels) transplantation of day-28 particles into the joints of SCID rats following particle induction by the protocol of the present invention.
Figure 13C:
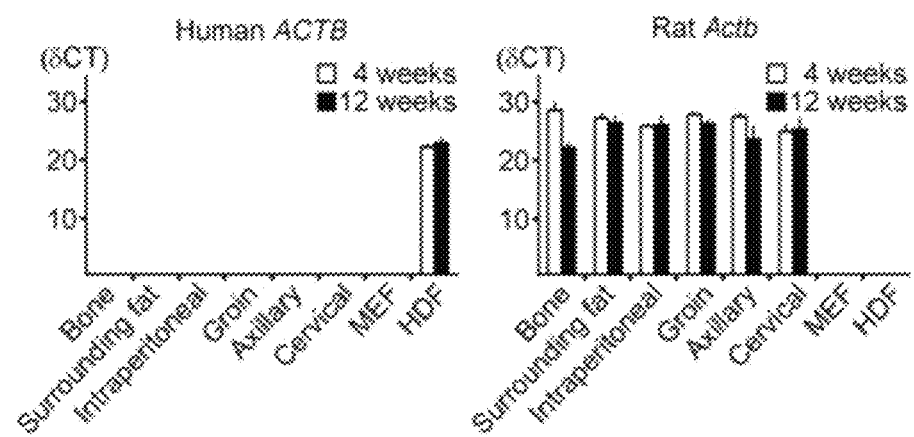
FIG. 13C shows the results of RT-PCR analysis of the expressions of human β-activin (ACTB) and rat β-activin (Actb) in tissues 4 or 12 weeks after transplantation of day-28 particles into the joints of SCID rats following particle induction by the protocol of the present invention.

Shallow defect sites were created in the articular cartilage of the SCID rats, and the human iPS cell-derived chondrocytes obtained on day 42 were transplanted into the defect sites. The mature chondrocyte particles obtained on day 42 were lubricious and unsuitable for transplantation into the shallow defect sites in the articular cartilage of the rats, and accordingly the chondrocyte particles obtained on day 28 were used. In three of four knee joints subjected to transplantation, the transplanted cells were survived 4 weeks after transplantation, as indicated by histological staining (FIG. 13A). Integration between the transplanted cells and the rat articular cartilage was strongly achieved (FIG. 13B). There were no tumor formation and no signs of metastasis at any of the four transplanted sites 4 or 12 weeks after transplantation (FIG. 13C). The results suggest that the day-28 particles of the human iPS cell-derived chondrocytes are suitable for transplantation. For deep defects, mature particles obtained on day 42 can be used.

The invention claimed is:

1. A method for producing chondrocytes from pluripotent stem cells, the method comprising the steps of:

(i) inducing pluripotent stem cells to differentiate into mesodermal cells in adherent culture, (ii) culturing the cells obtained by step (i) in adherent culture in a medium containing an effective amount of ascorbic acid, bone morphogenetic protein 2 (BMP2), transforming growth factor beta (TGFβ) and growth differentiation factor 5, (GDF5), and (iii) culturing the cells obtained by step (ii) in suspension culture in the medium containing ascorbic acid, BMP2, TGFβ and GDF5, thereby producing chondrocytes;

wherein the induction of differentiation into mesodermal cells in step (i) is achieved by culturing in a medium containing an effective amount of wingless-type MMTV integration site family, member 3A (Wnt3a) and Activin A.

2. The method of claim 1, further comprising the step of culturing the cells obtained by step (iii) in a serum-containing medium.

3. The method of claim 1, wherein the medium used in the steps (i), (ii) and (iii) further contains 1% fetal bovine serum (FBS).

4. The method of claim 1, wherein the culture in step (iii) is suspension culture of the cells obtained by step (ii) without prior use of a detachment solution comprising protease activity.

5. The method of claim 1, wherein step (i) takes 5 days or less.

6. The method of claim 1, wherein step (ii) takes 15 days or less.

7. The method of claim 1, wherein step (iii) takes 10 to 30 days.

8. The method of claim 5, wherein step (i) takes 3 days.

9. The method of claim 6, wherein step (ii) takes 11 days.

10. The method of claim 7, wherein step (iii) takes 14 to 28 days.

* * * * *